United States Patent [19]

Takebayashi et al.

[11] Patent Number: 5,387,596
[45] Date of Patent: Feb. 7, 1995

[54] BENZYLIDENETHIAZOLIDINE DERIVATIVES AND THEIR USE FOR THE INHIBITION LIPID PEROXIDES

[75] Inventors: Toyonori Takebayashi; Takayuki Onodera; Kazuo Hasegawa; Takashi Fujita; Takao Yoshioka, all of Hiromachi, Japan

[73] Assignee: Sankyo Company, Limited, Tokyo, Japan

[21] Appl. No.: 95,311

[22] Filed: Jul. 21, 1993

Related U.S. Application Data

[63] Continuation of Ser. No. 687,431, Apr. 18, 1991, abandoned.

[30] Foreign Application Priority Data

Apr. 27, 1990 [JP] Japan .................................. 2-113566

[51] Int. Cl.⁶ .................... A61K 31/425; C07D 417/12
[52] U.S. Cl. .................................. 514/369; 514/233.5; 514/320; 514/327; 544/133; 546/196; 548/183
[58] Field of Search ................ 544/133; 546/196, 269; 548/183; 514/233.5, 320, 327, 369

[56] References Cited

U.S. PATENT DOCUMENTS

| | | | |
|---|---|---|---|
| 4,287,200 | 9/1981 | Kawamatsu et al. | 548/183 |
| 4,572,912 | 2/1986 | Yoshioka et al. | 514/369 |
| 4,687,777 | 8/1987 | Meguro et al. | 514/342 |
| 4,873,255 | 10/1989 | Yoshioka et al. | 514/369 |
| 4,933,355 | 6/1990 | Yoshioka et al. | 514/369 |

FOREIGN PATENT DOCUMENTS 0008203  2/1980  European Pat. Off. .

OTHER PUBLICATIONS

Clark, WO 8651, (Sep. 1989).

*Primary Examiner*—Robert W. Ramsuer
*Attorney, Agent, or Firm*—Frishauf, Holtz, Goodman & Woodward

[57] ABSTRACT

Benzylidenethiazolidine compounds of formula (I):

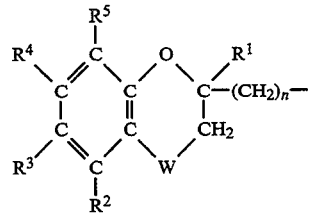

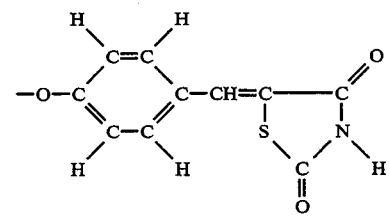

[in which $R^1$, $R^2$ and $R^5$ are each hydrogen or alkyl; $R^3$ and $R^4$ are each hydrogen, alkyl, formyl, alkylcarbonyl, arylcarbonyl, carboxy, alkoxycarbonyl, aryloxycarbonyl, hydroxy, alkylcarbonyloxy, formyloxy, arylcarbonyloxy, optionally substituted alkoxy or halogen; W is methylene, carbonyl or a group of formula $>C=N-OV$, wherein V is hydrogen, alkylcarbonyl, arylcarbonyl or optionally substituted alkyl; and $\underline{n}$ is an integer of from 1 to 3] and salts thereof have the ability to inhibit the formation of lipid peroxide in the mammalian body, and can therefore be used for the treatment of arteriosclerosis and other diseases and disorders arising from an imbalance in the lipid peroxide level. They can also be used for the preparation of the corresponding benzylthiazolidine compounds, which have a generally greater hypoglycemic activity. Processes for the preparation of these compounds of formula (I) are also provided.

5 Claims, No Drawings

BENZYLIDENETHIAZOLIDINE DERIVATIVES AND THEIR USE FOR THE INHIBITION LIPID PEROXIDES

This application is a continuation, of application Ser. No. 07/687,431, filed Apr. 18, 1991 (abandoned).

BACKGROUND TO THE INVENTION

The present invention relates to a series of novel benzylidenethiazolidine derivatives which have the ability to inhibit the formation of lipid peroxide in the mammalian body, to the use of these compounds for the treatment of arteriosclerosis and other diseases and disorders arising from an imbalance in the lipid peroxide level, to processes for the preparation of these compounds and to processes using these compounds for the preparation of other active compounds.

Certain thiazolidinone derivatives having the ability to lower blood lipid and blood glucose levels are disclosed in U.S. Pat. No. 4,572,912 and in U.S. patent application Ser. No. 833,867 filed the 25th day of Feb. 1986. Other thiazolidinone derivatives having a similar type of activity are disclosed in European Pat. No. 8203; but such compounds are structurally less similar to those of the present invention. However, the closest prior art of which we are presently aware is U.S. Pat. No. 4,873,255, which discloses a series of compounds which differ from those of the present invention in that they are benzylthiazolidine derivatives, rather than the benzylidenethiazolidine derivatives of the present invention.

We have now discovered a series of novel benzylidenethiazolidine derivatives which not only have the ability to inhibit the activity of lipid peroxide in the mammalian metabolism, but which also are of considerable value in preparing cheaply, effectively and in relatively high yields the compounds of the aforementioned U.S. Pat. No. 4,873,255, which are at present thought to be of greater value for their therapeutic activity.

BRIEF SUMMARY OF INVENTION

Thus, the compounds of the present invention may be represented by the formula (I):

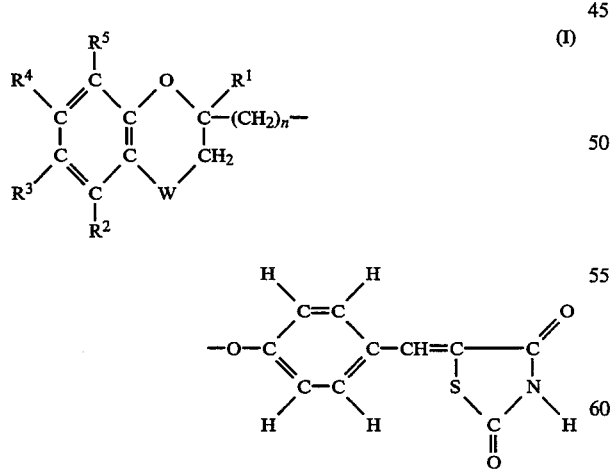

in which $R^1$, $R^2$ and $R^5$ are independently selected from the group consisting of hydrogen atoms and alkyl groups having from 1 to 10 carbon atoms;

$R^3$ and $R^4$ are independently selected from the group consisting of: hydrogen atoms; alkyl groups having from 1 to 10 carbon atoms; formyl groups; alkylcarbonyl groups having from 2 to 11 carbon atoms; arylcarbonyl groups in which the aryl part has from 6 to 10 ring carbon atoms and is unsubstituted or is substituted by at least one substituent selected from the group consisting of substituents (a), defined below; carboxy groups; alkoxycarbonyl groups having from 2 to 7 carbon atoms; aryloxycarbonyl groups in which the aryl part has from 6 to 10 ring carbon atoms and is unsubstituted or is substituted by at least one substituent selected from the group consisting of substituents (a), defined below; hydroxy groups; alkylcarbonyloxy groups having from 2 to 11 carbon atoms; formyloxy groups; arylcarbonyloxy groups in which the aryl part has from 6 to 10 ring carbon atoms and is unsubstituted or is substituted by at least one substituent selected from the group consisting of substituents (a), defined below; alkoxy groups having from 1 to 5 carbon atoms; substituted alkoxy groups having from 1 to 5 carbon atoms and substituted by at least one substituent selected from the group consisting of substituents (b), defined below; and halogen atoms;

W represents a methylene group ($>CH_2$), a carbonyl group ($>C=O$) or a group of formula $>C=N-OV$ wherein V represents: a hydrogen atom; an alkylcarbonyl group having from 2 to 6 carbon atoms; an arylcarbonyl group in which the aryl part has from 6 to 10 ring carbon atoms and is unsubstituted or is substituted by at least one substituent selected from the group consisting of substituents (a), defined below; an alkyl group having from 1 to 5 carbon atoms; a substituted alkyl group having from 1 to 5 carbon atoms and substituted by at least one substituent selected from the group consisting of substituents (d), defined below; and n is an integer of from 1 to 3;

substituents (a):
alkyl groups having from 1 to 5 carbon atoms; alkoxy groups having from 1 to 5 carbon atoms; and halogen atoms;

substituents (b):
aryl groups which have from 6 to 10 ring carbon atoms and which are unsubstituted or which have at least one substituent selected from the group consisting of substituents (a), defined above; carboxy groups; alkoxycarbonyl groups having from 2 to 6 carbon atoms; and groups of formula $-CONR^6R^7$, where $R^6$ and $R^7$ are independently selected from the group consisting of: hydrogen atoms; alkyl groups having from 1 to 5 carbon atoms; and aryl groups which have from 6 to 10 ring carbon atoms and which are unsubstituted or which have at least one substituent selected from the group consisting of substituents (a), defined above; or $R^6$ and $R^7$, together with the nitrogen atom to which they are attached, form a heterocyclic group which has from 3 to 7 ring atoms, of which 1 is said nitrogen atom and 0 or 1 is an additional hetero-atom selected from the group consisting of nitrogen, oxygen and sulfur hetero-atoms, said heterocyclic group being unsubstituted or being substituted by at least one substituent selected from the group consisting of substituents (c), defined below;

substituents (c):
alkyl groups having from 1 to 5 carbon atoms; and aryl groups which have from 6 to 10 ring carbon atoms and which are unsubstituted or which have at least one substituent selected from the group consisting of substituents (a), defined above;

substituents (d):
carboxy groups and alkoxycarbonyl groups having from 2 to 6 carbon atoms;

and pharmaceutically acceptable salts thereof.

The invention still further provides a pharmaceutical composition for the treatment or prophylaxis of diseases and disorders arising from an imbalance in the lipid peroxide level, said composition comprising an effective amount of a compound of formula (I) or a pharmaceutically acceptable salt thereof in admixture with a pharmaceutically acceptable carrier or diluent.

The invention still further provides a method of reducing lipid peroxide levels in an animal, especially a mammal, e.g. a human being, by administering to said animal an effective amount of a compound of formula (I) or a pharmaceutically acceptable salt thereof.

The invention still further provides processes for preparing the compounds of the invention and for using the compounds of the invention to prepare benzylthiazolidine derivatives, as described in greater detail hereafter.

DETAILED DESCRIPTION OF INVENTION

In the compounds of the present invention where $R^1$, $R^2$, $R^3$, $R^4$ or $R^5$ represents an alkyl group having from 1 to 10 carbon atoms, this may be a straight or branched chain alkyl group, and examples include the methyl, ethyl, propyl, isopropyl, butyl, isobutyl, sec-butyl, t-butyl, pentyl, isopentyl, neopentyl, 2-methylbutyl, 1-ethylpropyl, hexyl, neohexyl, 1-methylpentyl, 3-methylpentyl, 1,3-dimethylbutyl, 2-ethylbutyl, heptyl, 1-methylhexyl, 1-propylbutyl, 4,4-dimethylpentyl, octyl, 1-methylheptyl, 2-ethylhexyl, 5,5-dimethylhexyl, 1,1,3,3-tetramethylbutyl, nonyl, decyl, 1-methylnonyl, 3,7-dimethyloctyl and 7,7-dimethyloctyl groups. Of these, we prefer that $R^1$, $R^2$, $R^3$, $R^4$ and $R^5$ should represent a straight or branched chain alkyl group having from 1 to 4 carbon atoms. More preferably, where $R^1$, $R^2$, $R^3$ or $R^5$ represents an alkyl group, it is a methyl, ethyl, propyl, isopropyl, butyl or isobutyl group, and most preferably a methyl group. More preferably, where $R^4$ represents an alkyl group, it is a methyl, ethyl, propyl, isopropyl, butyl, isobutyl, sec-butyl or t-butyl group, and most preferably a methyl or t-butyl group, particularly a methyl group.

Where $R^3$ and/or $R^4$ represents an alkylcarbonyl group, this may be a straight or branched chain alkylcarbonyl group having from 2 to 11 carbon atoms. Examples of such alkylcarbonyl groups include the acetyl, propionyl, butyryl, isobutyryl, valeryl, isovaleryl, pivaloyl, hexanoyl, 2-methylpentanoyl, heptanoyl, isoheptanoyl, octanoyl, isooctanoyl, nonanoyl, 2-methyloctanoyl, isononanoyl, decanoyl and undecanoyl groups. Preferably, where $R^3$ and/or $R^4$ represents an alkylcarbonyl group, this is a straight or branched chain alkylcarbonyl group having from 2 to 7 carbon atoms, more preferably a straight or branched chain alkylcarbonyl group having from 2 to 5 carbon atoms, and most preferably an acetyl group.

Where $R^3$ and/or $R^4$ represents an arylcarbonyl group, whose aryl group has from 6 to 10 carbon atoms and may optionally have one or more substituents, it has, excluding any substituents, a total of from 7 to 11 carbon atoms. Examples of such groups include the benzoyl, 1-naphthoyl and 2-naphthoyl groups, which may be unsubstituted or substituted. Where the aryl moiety is substituted, we prefer that it should have from 1 to 5 substituents on the aromatic ring. These substituents are selected from the group consisting of substituents (a), and examples of such substituents include:

(1) straight and branched chain alkyl groups having from 1 to 5 carbon atoms, such as the methyl, ethyl propyl, isopropyl, butyl, isobutyl, sec-butyl, t-butyl, pentyl, isopentyl, neopentyl, 2-methylbutyl and 1-ethylpropyl groups;

(2) straight and branched chain alkoxy groups having from 1 to 5 carbon atoms, such as the methoxy, ethoxy, propoxy, isopropoxy, butoxy, isobutoxy, sec-butoxy, t-butoxy, pentyloxy and isopentyloxy groups; and (3) halogen atoms, such as the chlorine, fluorine and bromine atoms.

Examples of such groups which may be represented by $R^3$ and/or $R^4$ include: (a) the benzoyl, 1-naphthoyl and 2-naphthoyl groups; (b) the 4-methylbenzoyl, 2-propylbenzoyl, 3-butylbenzoyl, 4-pentylbenzoyl, 4-methyl-1-naphthoyl and 4-propyl-2-naphthoyl groups; (c) the 2-methoxybenzoyl, 4-ethoxybenzoyl, 4-butoxybenzoyl, 4-isopentyloxybenzoyl and 4-methoxy-1-naphthoyl groups; and (d) the 3-chlorobenzoyl, 4-fluorobenzoyl, 4-bromobenzoyl and 4-chloro-2-naphthoyl groups. Where $R^3$ and/or $R^4$ represents an arylcarbonyl group, this is preferably an arylcarbonyl group having from 7 to 11 carbon atoms whose aryl moiety has no substituents, and is most preferably a benzoyl group.

Where $R^3$ and/or $R^4$ represents an alkoxycarbonyl group, the alkoxy part may be a straight or branched chain group having from 1 to 6 carbon atoms, i.e. the alkoxycarbonyl group has from 2 to 7 carbon atoms. Examples of such alkoxycarbonyl groups include the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, neopentyloxycarbonyl, 2-methylbutoxycarbonyl, 1-ethylpropoxycarbonyl, hexyloxycarbonyl, neohexyloxycarbonyl, 1-methylpentyloxycarbonyl, 3-methylpentyloxycarbonyl, 1,3-dimethylbutoxycarbonyl and 2-ethylbutoxycarbonyl groups. Preferably $R^3$ represents a straight or branched chain alkoxycarbonyl group having from 2 to 5 carbon atoms and most preferably a methoxycarbonyl, ethoxycarbonyl or t-butoxycarbonyl group. Preferably $R^4$ represents a straight or branched chain alkoxycarbonyl group having from 2 to 5 carbon atoms.

Where $R^3$ and/or $R^4$ represents an aryloxycarbonyl group, whose aryl part has from 6 to 10 carbon atoms and may optionally have one or more substituents, it has, excluding any substituents, a total of from 7 to 11 carbon atoms. Examples of such groups include the phenoxycarbonyl, 1-naphthyloxycarbonyl and 2-naphthyloxycarbonyl groups, which may be unsubstituted or substituted. Where the aryl moiety is substituted, we prefer that it should have from 1 to 5 substituents on the aromatic ring. These substituents are selected from the group consisting of substituents (a), and examples of such substituents are as given above. Examples of such groups which may be represented by $R^3$ and/or $R^4$ include: (a) the phenoxycarbonyl, 1-naphthyloxycarbonyl and 2-naphthyloxycarbonyl groups; (b) the 4-methylphenoxycarbonyl, 2-propylphenoxycarbonyl, 3-butylphenoxycarbonyl, 4-pentylphenoxycarbonyl, 4-methyl-1-naphthyloxycarbonyl and 4-propyl-2-naphthyloxycarbonyl groups; (c) the 2-methoxyphenoxycarbonyl, 4-ethoxyphenoxycarbonyl, 4-butoxyphenoxycarbonyl, 4-isopentyloxyphenoxycarbonyl and 4-methoxy-1-naphthyloxycarbonyl groups; and (d) the 3-chlorophenoxycarbonyl, 4-fluorophenoxycarbonyl, 4-bromophenoxycarbonyl and 4-chloro-2-naphthyloxycarbonyl groups. Where $R^3$ and/or $R^4$ represents an aryloxycarbonyl group, this is preferably an aryloxycarbonyl group having from 7 to 11 carbon atoms whose aryl moiety has no substituents, and is most preferably a phenoxycarbonyl group.

Where $R^3$ and/or $R^4$ represents an alkylcarbonyloxy group, the alkyl part may be a straight or branched chain group having from 1 to 10 carbon atoms, i.e. the alkylcarbonyl group has from 2 to 11 carbon atoms. Examples of such alkylcarbonyloxy groups include the acetoxy, propionyloxy, butyryloxy, isobutyryloxy, valeryloxy, isovaleryloxy, pivaloyloxy, hexanoyloxy, 2-methylpentanoyloxy, heptanoyloxy, isoheptanoyloxy, octanoyloxy, isooctanoyloxy, nonanoyloxy, 2-methyloctanoyloxy, isononanoyloxy, decanoyloxy and undecanoyloxy groups. Where $R^3$ and/or $R^4$ represents an alkylcarbonyloxy group, this is preferably a straight or branched chain alkylcarbonyloxy group having from 2 to 7 carbon atoms, more preferably a straight or branched chain alkylcarbonyloxy group having from 2 to 5 carbon atoms, and most preferably an acetoxy group.

Where $R^3$ and/or $R^4$ represents an arylcarbonyloxy group, whose aryl group has from 6 to 10 carbon atoms and may optionally have one or more substituents, it has, excluding any substituents, a total of from 7 to 11 carbon atoms. Examples of such groups include the benzoyloxy, 1-naphthoyloxy and 2-naphthoyloxy groups, which may be unsubstituted or substituted. Where the aryl moiety is substituted, we prefer that it should have from 1 to 5 substituents on the aromatic ring. These substituents are selected from the group consisting of substituents (a), and examples of such substituents are as illustrated above. Examples of such groups which may be represented by $R^3$ and/or $R^4$ include: (a) the benzoyloxy, 1-naphthoyloxy and 2-naphthoyloxy groups; (b) the 4-methylbenzoyloxy, 2-propylbenzoyloxy, 3-butylbenzoyloxy, 4-pentylbenzoyloxy, 4-methyl-1-naphthoyloxy and 4-propyl-2-naphthoyloxy groups; (c) the 2-methoxybenzoyloxy, 4-ethoxybenzoyloxy, 4-butoxybenzoyloxy, 4-isopentyloxybenzoyloxy and 4-methoxy-1-naphthoyloxy groups; and (d) the 3-chlorobenzoyloxy, 4-fluorobenzoyloxy, 4-bromobenzoyloxy and 4-chloro-2-naphthoyloxy groups. Where $R^3$ and/or $R^4$ represents an arylcarbonyloxy group, this is preferably an arylcarbonyloxy group having from 7 to 11 carbon atoms whose aryl moiety has no substituents, and most preferably a benzoyloxy group.

Where $R^3$ and/or $R^4$ represents an alkoxy group, this may be a straight or branched chain alkoxy group having from 1 to 5 carbon atoms and it may be unsubstituted or it may have one or more substituents selected from the group consisting of substituents (b), defined above and exemplified below. Examples of such groups include the methoxy, ethoxy, propoxy, isopropoxy, butoxy, isobutoxy, sec-butoxy, t-butoxy, pentyloxy and isopentyloxy groups, which may be unsubstituted or may be substituted by one or more of substituents (b). Although the number of substituents is, in principle, limited only by the number of substitutable positions and possibly by steric constraints, in practice, we normally prefer from 1 to 3 substituents. Examples of such substituents include:

(1) aryl groups which may be unsubstituted or may have one or more substituents; these may be as defined above in relation to the aryl groups which may be represented by $R^3$ and R4; examples include the phenyl, 1-naphthyl and 2-naphthyl groups, which may be unsubstituted or may be substituted, preferably with from 1 to 5 substituents, as defined above;

(2) carboxy groups;

(3) alkoxycarbonyl groups having from 2 to 6 carbon atoms, which may be straight or branched chain groups, for example the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, neopentyloxycarbonyl, 2-methylbutoxycarbonyl and 1-ethylpropoxycarbonyl groups;

(4) groups of formula —$CONR^6R^7$ (wherein $R^6$ and $R^7$ are the same or different and each represents:

a hydrogen atom, a straight or branched chain alkyl group having from 1 to 5 carbon atoms, such as the methyl, ethyl, propyl, isopropyl, butyl, isobutyl, sec-butyl, t-butyl, pentyl, isopentyl, neopentyl, 2-methylbutyl and 1-ethylpropyl groups, an aryl group which may be unsubstituted or may be substituted by one or more of substituents (a), defined and exemplified above, and which has from 6 to 10 carbon atoms, such as the phenyl, 1-naphthyl and 2-naphthyl groups and substituted analogs thereof, as exemplified above, $R^6$ and $R^7$, together with the nitrogen atom to which they are attached, may form a heterocyclic ring, as defined and exemplified below.

The heterocyclic group which may be formed by the —$NR^6R^7$ part of the group of formula —$CONR^6R^7$ has from 3 to 7 ring atoms and is preferably a saturated group, which may optionally contain an additional oxygen, sulfur or nitrogen atom in the ring. The group may be unsubstituted or it may be substituted by at least one of substituents (c), defined above and exemplified below, in particular, where the heterocyclic group contains an additional nitrogen atom, the nitrogen atom may optionally be substituted; examples of these substituents include:

(i) straight or branched chain alkyl groups having from 1 to 5 carbon atoms, such as the methyl, ethyl, propyl, isopropyl, butyl, isobutyl, sec-butyl, t-butyl, pentyl, isopentyl, neopentyl, 2-methylbutyl and 1-ethylpropyl groups, and (ii) aryl groups which may optionally be substituted by one or more of substituents (a) and which, excluding any substituents, have from 6 to 10 carbon atoms, such as the phenyl, 1-naphthyl and 2-naphthyl group, and such groups having one or more substituents, as defined and exemplified above in relation to $R^3$ and $R^4$.

Examples of these heterocyclic groups include the 1-pyrrolidinyl, piperidino, morpholino, piperazinyl, N-methylpiperazinyl, N-phenylpiperazinyl, N-(4-methylphenyl)piperazinyl, N-(3-methoxyphenyl)piperazinyl and N-(2-chlorophenyl) piperazinyl groups.

Examples of the substituted and unsubstituted alkoxy groups which may be represented by $R^3$ or $R^4$ include: (a) the methoxy, ethoxy, propoxy, isopropoxy, butoxy, isobutoxy, sec-butoxy, t-butoxy, pentyloxy and isopentyloxy groups, (b) the benzyloxy, phenethyloxy, 3-phenylpropoxy, α-naphthylmethoxy and β-naphthylmethoxy groups, (c) the 4-methylbenzyloxy, 4-butylbenzyloxy, 4-ethylphenethyloxy and 5-methyl-α-naphthylmethoxy groups, (d) the 4-methoxybenzyloxy, 4-ethoxybenzyloxy, 4-butoxyphenethyloxy and 5-methoxy-α-naphthylmethoxy groups, (e) the 4-chlorobenzyloxy, 4-bromobenzyloxy, 4-fluorophenethyloxy and 5-chloro-α-napthylmethoxy groups, (f) the carboxymethoxy, 2-carboxyethoxy, 3-carboxypropoxy, 3-carboxybutoxy, 3-carboxy-1-methylpropoxy and 1-carboxy-1-methylethoxy groups, (g) the methoxycarbonylmethoxy, 3-methoxycarbonylpropoxy, 2-propoxycarbonylethoxy, 3-pentyloxycarbonylpropoxy, 4-butoxycarbonylbutoxy, 3-methoxycarbonyl-1-methylpropoxy, 1-methoxycarbonyl-1-methylethoxy, t-butoxycarbonylmethoxy, 3-(t-butoxycarbonyl)propoxy and 1-(t-butoxycarbonyl)-1-methylethoxy groups, (h) the carbamoylmethoxy, 2-carbamoylethoxy and 4-carbamoylbutoxy groups, (i) the methylaminocarbonylmethoxy, 2-propylaminocarbonylethoxy, 3-(N,N-dimethylaminocarbonyl)propoxy, 4-N-methyl-N-ethylaminocarbonyl)butoxy and 3-(N,N-dipentylaminocarbonyl)-1-methylpropoxy groups, (j) the phenylaminocarbonylmethoxy, 2-phenylaminocarbonylethoxy, 3-phenylaminocarbonylpropoxy, 4-phenylaminocarbonylbutoxy and 3-phenylaminocarbonyl-1-methylpropoxy groups, (k) the 4-methylphenylaminocarbonylmethoxy and 2-(4-propylphenylaminocarbonyl)ethoxy groups, (l) the 3-(3-ethoxyphenylaminocarbonyl)propoxy and 4-(3-butoxyphenylaminocarbonyl)butoxy groups, (m) the 4-chlorophenylaminocarbonylmethoxy and 3-(4-fluorophenylaminocarbonyl)-1-methylpropoxy groups, (n) the 1-pyrrolidinylcarbonylmethoxy, piperidinocarbonylmethoxy, morpholinocarbonylmethoxy, 2-(piperazinylcarbonyl)ethoxy, 2-(piperidinocarbonyl)ethoxy and 4-(morpholinocarbonyl)butoxy groups, (o) the N-methylpiperazinylcarbonylmethoxy group, (p) the N-phenylpiperazinylcarbonylmethoxy group, (q) the N-(4-methylphenyl)piperazinylcarbonylmethoxy group, (r) the N-(3-methoxyphenyl)piperazinylcarbonylmethoxy group and (s) the N-(2-chlorophenyl)piperazinylcarbonylmethoxy group. Where $R^3$ and/or $R^4$ represents an optionally substituted alkoxy group, this is preferably a straight or branched chain alkoxy group having from 1 to 3 carbon atoms, which is unsubstituted or has one or two substituents, the substituents being selected from the group consisting of:

[1] aryl groups having from 6 to 10 carbon atoms and without any substituent on the aromatic ring;

[2] carboxy groups;

[3] straight or branched chain alkoxycarbonyl groups having from 2 to 5 carbon atoms;

[4] carbamoyl groups; and

[5] groups of formula —CONR$^{6'}$R$^{7'}$ (wherein R$^{6'}$ and R$^{7'}$, together with the nitrogen atom to which they are attached, form a saturated heterocyclic ring having from 5 to 7 ring atoms, which may contain an additional oxygen or nitrogen atom in the ring, and which has no substituents.

$R^3$ more preferably represents a methoxy, benzyloxy, carboxymethoxy, 3-carboxypropoxy, 1-carboxy-1-methylethoxy, methoxycarbonylmethoxy, 3-methoxycarbonylpropoxy, 1-methoxycarbonyl-1-methylethoxy, t-butoxycarbonylmethoxy, 3-(t-butoxycarbonyl)propoxy, 1-(t-butoxycarbonyl)-1-methylethoxy, carbamoylmethoxy, piperidinocarbonylmethoxy or morpholinocarbonylmethoxy group, and most preferably represents a methoxy, benzyloxy, carboxymethoxy, 3-carboxypropoxy or 1-carboxy-1-methylethoxy group. $R^4$ more preferably represents a carboxymethoxy, benzyloxy, 3-carboxypropoxy, 1-carboxy-1-methylethoxy, methoxycarbonylmethoxy, 3-methoxycarbonylpropoxy, 1-methoxycarbonyl-1-methylethoxy, t-butoxycarbonylmethoxy, 3-(t-butoxycarbonyl)propoxy or 1-(t-butoxycarbonyl)-1-methylethoxy group, and most preferably a carboxymethoxy, 3-carboxypropoxy or 1-carboxy-1-methylethoxy group.

Where $R^3$ and/or $R^4$ represents a halogen atom, this may preferably be a chlorine, fluorine or bromine atom. In this case, $R^3$ and/or $R^4$ preferably represents a chlorine or fluorine atom, and most preferably a fluorine atom.

Where V represents an alkylcarbonyl group, this may be a straight or branched chain alkylcarbonyl group having from 2 to 6 carbon atoms such as, for example, an acetyl, propionyl, butyryl or hexanoyl group. In this case, V preferably represents a straight or branched chain alkylcarbonyl group having from 2 to 4 carbon atoms, and most preferably an acetyl group.

Where V represents an arylcarbonyl group, it may be an arylcarbonyl group having from 7 to 11 carbon atoms, i.e. the aryl group itself (without substituents) has from 6 to 10 carbon atoms, and examples include the benzoyl, 1-naphthoyl and 2-naphthoyl groups. Such groups may be substituted or unsubstituted and, if substituted, may have one or more, preferably from 1 to 5, of substituents (a), as defined and exemplified above. Examples of such groups which may be represented by V include: (a) the benzoyl, 1-naphthoyl and 2-naphthoyl groups; (b) the 4-methylbenzoyl, 2-propylbenzoyl, 3-butylbenzoyl, 4-pentylbenzoyl, 4-methyl-1-naphthoyl and 4-propyl-2-naphthoyl groups; (c) the 2-methoxybenzoyl, 4-ethoxybenzoyl, 4-butoxybenzoyl, 4-isopentyloxybenzoyl and 4-methoxy-1-naphthoyl groups; and (d) the 3-chlorobenzoyl, 4-fluorobenzoyl, 4-bromobenzoyl and 4-chloro-2-naphthoyl groups. Where V represents an arylcarbonyl group, this is more preferably an arylcarbonyl group having from 7 to 11 carbon atoms whose aryl moiety has no substituents, and most preferably a benzoyl group.

Where V represents an alkyl group, this may be a straight or branched chain alkyl group having from 1 to 5 carbon atoms and optionally substituted by one or more of substituents (d). Although there is no particular limitation on the number of substituents on the alkyl group, from one to three substituents are preferred. Examples of the unsubstituted groups include the methyl, ethyl, propyl, isopropyl, butyl, isobutyl, sec-butyl, t-butyl, pentyl, isopentyl, neopentyl, 2-methylbutyl and 1-ethylpropyl groups. The substituted group may be any of these unsubstituted groups but substituted by one or more of substituents (d). Examples of the substituents include:

(1) carboxy groups; and (2) straight and branched chain alkoxycarbonyl groups having from 2 to 6 carbon atoms such as the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, neopentyloxycarbonyl, 2-methylbutoxycarbonyl and 1-ethylpropoxycarbonyl groups.

Examples of such substituted and unsubstituted groups which may be represented by V include: (a) the methyl, ethyl, propyl, isopropyl, butyl, isobutyl, sec-butyl, t-butyl, pentyl, isopentyl, neopentyl, 2-methylbutyl and 1-ethylpropyl groups, (b) the carboxymethyl, 2-carboxyethyl, 3-carboxypropyl, 3-carboxybutyl, 3-carboxy-1-methylpropyl and 1-carboxy-1-methylethyl groups, and (c) the methoxycarbonylmethyl, 3-methoxycarbonylpropyl, ethoxycarbonylmethyl, 3-ethoxycarbonylpropyl, 2-propoxycarbonylethyl, 3-pentyloxycarbonylpropyl, 4-butoxycarbonylbutyl, 3-methoxycarbonyl-1-methylpropyl, 1-methoxycarbonyl-1-methylethyl, t-butoxycarbonylmethyl, 3-(t-butoxycarbonyl)propyl and 1-(t-butoxycarbonyl)-1-methylethyl groups.

The symbol n represents an integer of from 1 to 3, and is preferably 1 or 2, and most preferably 1.

The compounds of the present invention can form salts with bases. There is no particular restriction on the nature of these salts, provided that, where they are intended for therapeutic use, they are pharmaceutically acceptable. Where they are intended for non-therapeutic uses, e.g. as intermediates in the preparation of other, and possibly more active, compounds, even this restriction does not apply. Examples of such salts include: salts with an alkali metal, such as sodium, potassium or lithium; salts with an alkaline earth metal, such as barium or calcium; salts with another metal, such as magnesium or aluminum; organic base salts, such as a salt with dicyclohexylamine; and salts with a basic amino acid, such as lysine or arginine. Depending on the nature of the substituent groups, the compounds of the present invention may contain one or more, e.g. one, two or three carboxy groups, and, accordingly, where the cation is monobasic, the salts may be a mono-, di- or tri-salt. Pharmaceutically acceptable salts are preferred.

The compounds of the present invention have an asymmetric carbon atom at the 2-position of the chroman ring and can thus form optical isomers. They also have a double bond in the benzylidene moiety and can therefore form geometrical isomers. Moreover, certain of the substituent groups may contain one or more asymmetric carbon atoms in their molecules, and can thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques. In the process, method and composition of the invention, the individual isomers or a mixture of isomers may be used.

In addition, all of the compounds of the present invention may exist in the form of tautomers, as represented below [in which, for the sake of clarity, only the thiazolidinedione or equivalent part of the molecule is shown, the remainder being as in formula (I)]:

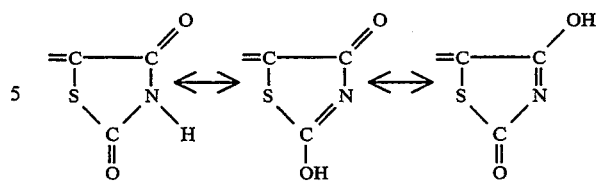

Each of these tautomers individually forms a part of this invention, although all are represented herein by a single formula, and, in practice, any specific compound may normally be expected to be a mixture of all tautomers.

The preferred compounds of the present invention are those compounds of formula (I) in which:

(i) $R^1$ represents a hydrogen atom or a straight or branched chain alkyl group having from 1 to 10 carbon atoms.

(ii) $R^2$ represents a hydrogen atom or a straight or branched chain alkyl group having from 1 to 10 carbon atoms.

(iii) $R^3$ and $R^4$ are the same or different and each represents:
(A) a hydrogen atom;
(B) a straight or branched chain alkyl group having from 1 to 10 carbon atoms;
(C) a formyl group;
(D) a straight or branched chain alkylcarbonyl group having from 2 to 11 carbon atoms;
(E) an arylcarbonyl group having from 7 to 11 carbon atoms which is unsubstituted or has from one to five substituents, the substituents being selected from the group consisting of (1) alkyl groups having from 1 to 5 carbon atoms, (2) alkoxy groups having from 1 to 5 carbon atoms and (3) halogen atoms;
(F) a carboxy group;
(G) a straight or branched chain alkoxycarbonyl group having from 2 to 7 carbon atoms;
(H) an aryloxycarbonyl group having from 7 to 11 carbon atoms;
(I) a hydroxy group;
(J) a straight or branched chain alkylcarbonyloxy group having from 2 to 11 carbon atoms;
(K) an arylcarbonyloxy group having from 7 to 11 carbon atoms, whose aryl moiety is unsubstituted or has from one to five substituents, the substituents being selected from the group consisting of
(1) straight or branched chain alkyl groups having from 1 to 5 carbon atoms,
(2) straight or branched chain alkoxy groups having from 1 to 5 carbon atoms and
(3) halogen atoms;
(L) a straight or branched chain alkoxy group having from 1 to 5 carbon atoms which is unsubstituted or has from one to three substituents, the substituents being selected from the group consisting of
(1) aryl groups having from 6 to 10 carbon atoms which themselves are unsubstituted or have from one to five substituents on the aromatic ring, the substituents being selected from the group consisting of (a) straight or branched chain alkyl groups having from 1 to 5 carbon atoms, (b) straight or branched chain alkoxy groups having from 1 to 5 carbon atoms and (c) halogen atoms, (2) carboxy groups, (3) straight or branched chain alkoxycarbonyl groups having from 2 to 6 carbon atoms, (4) groups of formula —CONR$^6$R$^7$, wherein R$^6$ and R$^7$ are the same or different and each represents
[1] a hydrogen atom,
[2] a straight or branched chain alkyl group having from 1 to 5 carbon atoms,
[3] an aryl group having from 6 to 10 carbon atoms which is unsubstituted or has from one to five substituents on the aromatic ring, the substituents being selected from the group consisting of (i) straight or branched chain alkyl groups having from 1 to 5 carbon atoms, (ii) straight or branched chain alkoxy groups having from 1 to 5 carbon atoms and (iii) halogen atoms, or
[4] R$^6$ and R$^7$, together with the nitrogen atom to which they are attached, form a saturated heterocyclic group having from 3 to 7 ring atoms, of which 1 is said nitrogen atom and 0 or 1 is an additional oxygen or nitrogen atom, the group being unsubstituted or being substituted by at least one substituent, the substituent being selected from the group consisting of (i) straight or branched chain alkyl groups having from 1 to 5 carbon atoms and (ii) aryl groups having from 6 to 10 carbon atoms, which themselves are unsubstituted or are substituted by from 1 to 5 substituents, the substituents being selected from the group consisting of (a) straight or branched chain alkyl groups having from 1 to 5 carbon atoms, (b) straight or branched chain alkoxy groups having from 1 to 5 carbon atoms and (c) halogen atoms; or (M) a halogen atom.

(iv) R$^5$ represents a hydrogen atom or a straight or branched chain alkyl group having from 1 to 10 carbon atoms.

(v) W represents a methylene group, a carbonyl group, or a group of formula >C=N—OV, wherein V represents:
(1) a hydrogen atom,
(2) a straight or branched chain alkylcarbonyl group having from 2 to 6 carbon atoms,
(3) an arylcarbonyl group having from 7 to 11 carbon atoms, or
(4) a straight or branched chain alkyl group having from 1 to 5 carbon atoms, said group being unsubstituted or being substituted by from one to three substituents, the substituents being selected from the group consisting of
[1] carboxy groups and
[2] straight or branched chain alkoxycarbonyl groups having from 2 to 6 carbon atoms.

(vi) $n$ is 1 or 2.

In particular, of these, we prefer those compounds of formula (I) in which R$^1$ is as defined in (i) above; R$^2$ is as defined in (ii) above; R$^3$ and R$^4$ are as defined in (iii) above; R$^5$ is as defined in (iv) above; W is as defined in (v) above; and $n$ is as defined in (vi) above.

The more preferred compounds of the present invention are those compounds of formula (I) in which:

(vii) R$^1$ represents a hydrogen atom or a straight or branched chain alkyl group having from 1 to 4 carbon atoms.

(viii) R$^2$ represents a hydrogen atom or a straight or branched chain alkyl group having from 1 to 4 carbon atoms.

(ix) R$^3$ and R$^4$ are the same or different and each represents:
(A) a hydrogen atom;
(B) a straight or branched chain alkyl group having from 1 to 4 carbon atoms;
(C) a straight or branched chain alkylcarbonyl group having from 2 to 7 carbon atoms;
(D) an arylcarbonyl group having from 7 to 11 carbon atoms and whose aryl moiety is unsubstituted;
(E) a carboxy group;
(F) a straight or branched chain alkoxycarbonyl group having from 2 to 5 carbon atoms;
(G) a hydroxy group;
(H) a straight or branched chain alkylcarbonyloxy group having from 2 to 7 carbon atoms;
(I) an arylcarbonyloxy group having from 7 to 11 carbon atoms and whose aryl moiety is unsubstituted,
(J) a straight or branched chain alkoxy group having from 1 to 3 carbon atoms, said group being unsubstituted or being substituted by one or two substituents, the substituents being selected from the group consisting of
[1] aryl groups having from 6 to 10 carbon atoms and whose aryl moiety is unsubstituted,
[2] carboxy groups,
[3] straight or branched chain alkoxycarbonyl groups having from 2 to 5 carbon atoms,
[4] carbamoyl groups, and
[5] groups of formula —CONR$^{6'}$R$^{7'}$, wherein R$^{6'}$ and R$^{7'}$, together with nitrogen atom to which they are attached, form a saturated heterocyclic group having from 3 to 7 ring atoms, of which 1 is said nitrogen atom and 0 or 1 is an additional oxygen or nitrogen atom, the group being unsubstituted; and
(K) halogen atoms.

(x) R$^5$ represents a hydrogen atom or a straight or branched chain alkyl group having from 1 to 4 carbon atoms;

(xi) W represents a methylene group or a group of formula >C=N—OV
wherein V represents:
(1) a hydrogen atom,
(2) a straight or branched chain alkylcarbonyl group having from 2 to 4 carbon atoms, or
(3) a benzoyl group.

In particular, of these, we prefer those compounds of formula (I) and salts thereof in which R$^1$ is as defined in (vii) above, R$^2$ is as defined in (viii) above, R$^3$ and R$^4$ are as defined in (ix) above, R$^5$ is as defined in (x) above, W is as defined in (xi) above, and $n$ is as defined in (vi) above.

Still more preferred compounds of the present invention of the general formula (I) are those in which:

(xii) R$^1$ represents a hydrogen atom or a methyl, ethyl, propyl, isopropyl, butyl or isobutyl group.

(xiii) R$^2$ represents a hydrogen atom or a methyl, ethyl, propyl, isopropyl, butyl or isobutyl group.

(xiv) R$^3$ represents a hydrogen atom, a methyl, ethyl, propyl, isopropyl, butyl or isobutyl group, a straight or branched chain alkylcarbonyl group having from 2 to 5 carbon atoms, a benzoyl group, a carboxy group, a straight or branched chain alkoxycarbonyl group having from 2 to 5 carbon atoms, a hydroxy group, a straight or branched chain alkylcarbonyloxy group having from 2 to 5 carbon atoms, a benzoyloxy, methoxy, benzyloxy, carboxymethoxy, 3-carboxypropoxy, 1-carboxy-1-methylethoxy, methoxycarbonylmethoxy, 3-methoxycarbonylpropoxy, 1-methoxycarbonyl-1-methylethoxy, t-butoxycarbonylmethoxy, 3-(t-butoxycarbonyl)propoxy, 1-(t-butoxycarbonyl)-1-methylethoxy, carbamoylmethoxy, piperidinocarbonylmethoxy or morpholinocarbonylmethoxy group, or a chlorine or fluorine atom.

(xv) $R^4$ represents a hydrogen atom, a methyl, ethyl, propyl, isopropyl, butyl, isobutyl, sec-butyl or t-butyl group, a straight or branched chain alkylcarbonyl group having from 2 to 5 carbon atoms, a benzoyl group, a hydroxy group, a straight or branched chain alkylcarbonyloxy group having from 2 to 5 carbon atoms, an arylcarbonyloxy group having from 7 to 11 carbon atoms and whose aryl moiety is unsubstituted, a carboxymethoxy, 3-carboxypropoxy, 1-carboxy-1-methylethoxy, methoxycarbonylmethoxy, 3-methoxycarbonylpropoxy, 1-methoxycarbonyl-1-methylethoxy, t-butoxycarbonylmethoxy, 3-(t-butoxycarbonyl)propoxy or 1-(t-butoxycarbonyl)-1-methylethoxy group, or a chlorine or fluorine atom.

(xvi) $R^5$ represents a hydrogen atom, or a methyl, ethyl, propyl, isopropyl, butyl or isobutyl group.

(xvii) W represents a methylene group or a group of formula $>C=N-OV$, wherein V represents a hydrogen atom or an acetyl group.

In particular, of these, we prefer those compounds of formula (I) and salts thereof in which $R^1$ is as defined in (xii) above, $R^2$ is as defined in (xiii) above, $R^3$ is as defined in (xiv) above, $R^4$ is as defined in (xv) above, $R^5$ is as defined in (xvi) above, W is as defined in (xvii) above, and $\underline{n}$ is as defined in (vi) above.

The most preferred compounds of the present invention are those compounds of formula (I) in which:

(xviii) $R^1$ represents a methyl group.

(xix) $R^2$ represents a hydrogen atom or a methyl group.

(xx) $R^3$ represents a hydrogen atom, a methyl, acetyl, carboxy, methoxycarbonyl, ethoxycarbonyl, t-butoxycarbonyl, hydroxy, acetoxy, methoxy, benzyloxy, carboxymethoxy or 3-carboxypropoxy group, or a fluorine atom;

(xxi) $R^4$ represents a hydrogen atom, a methyl, t-butyl, acetyl, hydroxy, acetoxy, benzoyloxy, carboxymethoxy, 3-carboxypropoxy or 1-carboxy-1-methylethoxy group or a fluorine atom;

(xxii) $R^5$ represents a hydrogen atom or a methyl group.

(xxiii) W represents a methylene group.

(xxiv) $\underline{n}$ is 1.

In particular, of these, we prefer those compounds of formula (I) and salts thereof in which $R^1$ is as defined in (xviii) above, $R^2$ is as defined in (xix) above, $R^3$ is as defined in (xx) above, $R^4$ is as defined in (xxi) above, $R^5$ is as defined in (xxii) above, W is as defined in (xxiii) above, and $\underline{n}$ is as defined in (xxiv) above.

Specific examples of compounds of the present invention are shown by the following formulae (I-1) and (I-2), in which the substituent groups are as defined by the corresponding one of Tables 1 and 2, i.e. formula (I-1) relates to Table 1 and formula (I-2) relates to Table 2. In the Tables, the following abbreviations are used:

| | |
|---|---|
| Ac | acetyl |
| Boz | benzoyl |
| Bu | butyl |
| iBu | isobutyl |
| tBu | t-butyl |
| iByr | isobutyl |
| Bz | benzyl |
| Car | carbamoyl |
| Dc | decyl |
| Et | ethyl |
| Fo | formyl |
| Me | methyl |
| Mec | methoxycarbonyl |
| Mor | morpholino |
| Npo | naphthoyl |
| Oc | octyl |
| Ph | phenyl |
| Pip | piperidyl |
| Piv | pivaloyl |
| Pr | propyl |
| Prn | propionyl |
| Pyrd | pyrrolidinyl |
| Tmb | 1,1,3,3-tetramethylbutyl |
| Va | valeryl |

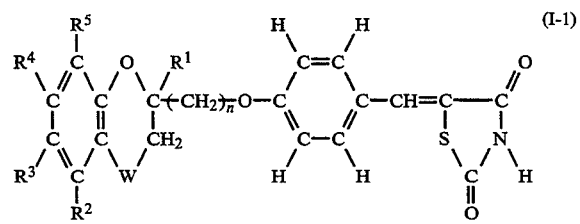

(I-1)

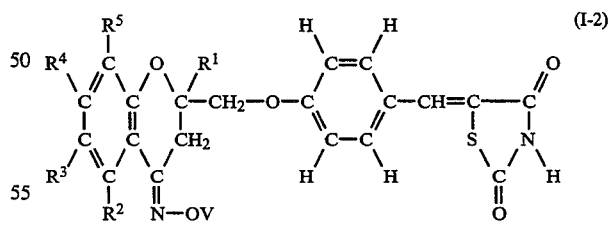

(I-2)

TABLE 1

| Cpd. No. | $R^1$ | $R^2$ | $R^3$ | $R^4$ | $R^5$ | W | $\underline{n}$ |
|---|---|---|---|---|---|---|---|
| 1-1 | H | H | H | H | H | $CH_2$ | 1 |
| 1-2 | Me | H | H | H | H | $CH_2$ | 1 |
| 1-3 | Me | H | H | H | H | $CH_2$ | 2 |
| 1-4 | Me | H | F | H | H | $CH_2$ | 1 |
| 1-5 | Me | H | Cl | H | H | $CH_2$ | 1 |
| 1-6 | Me | H | H | F | H | $CH_2$ | 1 |
| 1-7 | Me | Me | H | Me | H | $CH_2$ | 1 |
| 1-8 | Me | Me | Me | Me | Me | $CH_2$ | 1 |

TABLE 1-continued

| Cpd. No. | R¹ | R² | R³ | R⁴ | R⁵ | W | n |
|---|---|---|---|---|---|---|---|
| 1-9 | Me | H | H | HO | Me | $CH_2$ | 1 |
| 1-10 | Me | H | H | HO | Me | $CH_2$ | 2 |
| 1-11 | Me | H | H | HOOCCH$_2$O | Me | $CH_2$ | 1 |
| 1-12 | Me | H | H | HOOCCH$_2$O | Me | CO | 1 |
| 1-13 | Me | H | H | AcO | Me | $CH_2$ | 1 |
| 1-14 | Me | H | H | AcO | Me | CO | 1 |
| 1-15 | Me | H | H | BozO | Me | $CH_2$ | 1 |
| 1-16 | Me | H | H | BozO | Me | CO | 1 |
| 1-17 | Me | H | H | 3-HOOC—PrO | Me | $CH_2$ | 1 |
| 1-18 | Me | H | H | 3-EtOOC—PrO | Me | $CH_2$ | 1 |
| 1-19 | Me | H | H | HOOC—C(Me)$_2$—O— | Me | $CH_2$ | 1 |
| 1-20 | Me | H | H | Mec-C(Me)$_2$—O— | Me | $CH_2$ | 1 |
| 1-21 | Me | H | H | Car-CH$_2$O— | Me | $CH_2$ | 1 |
| 1-22 | Me | H | H | diMeCar-CH$_2$O— | Me | $CH_2$ | 1 |
| 1-23 | Me | H | H | 1-Pyrd-CO—CH$_2$O— | Me | $CH_2$ | 1 |
| 1-24 | Me | H | H | 3-(1-Pip-CO)PrO— | Me | $CH_2$ | 1 |
| 1-25 | Me | H | H | 3-(Mor-CO)PrO— | Me | $CH_2$ | 1 |
| 1-26 | Me | H | HO | H | H | $CH_2$ | 1 |
| 1-27 | Me | Me | HO | Me | Me | $CH_2$ | 1 |
| 1-28 | Me | Me | HO | Me | Me | $CH_2$ | 2 |
| 1-29 | Me | Me | HO | Me | Me | CO | 1 |
| 1-30 | Me | H | HO | tBu | H | $CH_2$ | 1 |
| 1-31 | Me | H | HO | Tmb | H | $CH_2$ | 1 |
| 1-32 | iBu | Me | HO | Me | Me | $CH_2$ | 1 |
| 1-33 | iBu | Me | HO | Me | Me | CO | 1 |
| 1-34 | Oc | Me | HO | Me | Me | $CH_2$ | 1 |
| 1-35 | Dc | Me | HO | Me | Me | $CH_2$ | 1 |
| 1-36 | 3,7-diMeOc | Me | HO | Me | Me | $CH_2$ | 1 |
| 1-37 | Me | Me | AcO | Me | Me | $CH_2$ | 1 |
| 1-38 | Me | Me | AcO | Me | Me | CO | 1 |
| 1-39 | Me | Me | BozO | Me | Me | $CH_2$ | 1 |
| 1-40 | Me | Me | MeO | Me | Me | $CH_2$ | 1 |
| 1-41 | Me | Me | BzO | Me | Me | $CH_2$ | 1 |
| 1-42 | Me | Me | PrO | Me | Me | $CH_2$ | 1 |
| 1-43 | H | H | HOOCCH$_2$O | H | H | $CH_2$ | 1 |
| 1-44 | Me | H | HOOC(CH$_2$)$_3$O | tBu | H | $CH_2$ | 1 |
| 1-45 | Me | Me | HOOCCH$_2$O | Me | Me | $CH_2$ | 1 |
| 1-46 | Me | Me | HOOCCH$_2$O | Me | Me | CO | 1 |
| 1-47 | Me | Me | EtOOCCH$_2$O | Me | Me | $CH_2$ | 1 |
| 1-48 | Me | Me | HOOC(CH$_2$)$_3$O | Me | Me | $CH_2$ | 1 |
| 1-49 | Me | Me | HOOC(CH$_2$)$_3$O | Me | Me | $CH_2$ | 2 |
| 1-50 | Me | Me | EtOOC(CH$_2$)$_3$O | Me | Me | $CH_2$ | 1 |
| 1-51 | Me | Me | tBuOOC(CH$_2$)$_3$O | Me | Me | $CH_2$ | 1 |
| 1-52 | Me | Me | HOOCC(Me)$_2$O | Me | Me | $CH_2$ | 1 |
| 1-53 | Me | Me | EtOOCC(Me)$_2$O | Me | Me | $CH_2$ | 1 |
| 1-54 | Me | Me | tBuOOCC(Me)$_2$O | Me | Me | $CH_2$ | 1 |
| 1-55 | H | H | CarCH$_2$O | Me | H | $CH_2$ | 1 |
| 1-56 | Me | Me | CarCH$_2$O | Me | Me | $CH_2$ | 1 |
| 1-57 | Me | Me | CarCH$_2$O | Me | Me | $CH_2$ | 2 |
| 1-58 | Me | Me | CarCH$_2$O | Me | Me | CO | 1 |
| 1-59 | Me | Me | diMeCarCH$_2$O | Me | Me | $CH_2$ | 1 |
| 1-60 | Me | Me | 1-Pyrd-CO—CH$_2$O— | Me | Me | $CH_2$ | 1 |
| 1-61 | Me | Me | 1-Pip-CO—CH$_2$O— | Me | Me | $CH_2$ | 1 |
| 1-62 | Me | Me | Mor-CO—CH$_2$O— | Me | Me | $CH_2$ | 1 |
| 1-63 | Me | Me | Mor-CO—CH$_2$O— | Me | Me | CO | 1 |
| 1-64 | Me | Me | Car(CH$_2$)$_3$O— | Me | Me | $CH_2$ | 1 |
| 1-65 | Me | Me | N-EtCar(CH$_2$)$_3$O— | Me | Me | $CH_2$ | 1 |
| 1-66 | Me | Me | N-Bu-N-MeCar(CH$_2$)$_3$O— | Me | Me | $CH_2$ | 1 |
| 1-67 | Me | Me | Mor-CO—(CH$_2$)$_3$O— | Me | Me | $CH_2$ | 1 |
| 1-68 | Me | Me | CarC(Me)$_2$O— | Me | Me | $CH_2$ | 1 |
| 1-69 | Me | Me | 1-Pyrd-CO—C(Me)$_2$O— | Me | Me | $CH_2$ | 1 |
| 1-70 | Me | H | HOOC— | H | H | $CH_2$ | 1 |
| 1-71 | Me | H | EtOOC— | H | H | $CH_2$ | 1 |
| 1-72 | Me | H | tBuOOC— | H | H | $CH_2$ | 1 |
| 1-73 | Me | H | PhOOC— | HOOC— | H | $CH_2$ | 1 |
| 1-74 | Me | H | H | HOOC— | H | $CH_2$ | 1 |
| 1-75 | Me | Me | Fo | Me | Me | $CH_2$ | 1 |
| 1-76 | Me | H | Ac | HO | Me | $CH_2$ | 1 |
| 1-77 | Me | H | Ac | HO | Me | CO | 1 |
| 1-78 | Me | H | Prn | HO | Me | $CH_2$ | 1 |
| 1-79 | Me | H | iByr | HO | Me | $CH_2$ | 1 |
| 1-80 | Me | H | Piv | HO | Me | $CH_2$ | 1 |
| 1-81 | Me | H | Boz | HO | Me | $CH_2$ | 1 |
| 1-82 | Me | H | 1-Npo | HO | Me | $CH_2$ | 1 |
| 1-83 | Me | H | Ac | AcO | Me | $CH_2$ | 1 |
| 1-84 | Me | H | Ac | BozO | Me | $CH_2$ | 1 |
| 1-85 | Me | H | Ac | 1-NpoO | Me | $CH_2$ | 1 |
| 1-86 | Me | H | Boz | AcO | Me | $CH_2$ | 1 |
| 1-87 | Me | H | p-MeBoz | PrnO | Me | $CH_2$ | 1 |
| 1-88 | Me | H | m-ClBoz | HO | Me | $CH_2$ | 1 |

TABLE 1-continued

| Cpd. No. | $R^1$ | $R^2$ | $R^3$ | $R^4$ | $R^5$ | W | $n$ |
|---|---|---|---|---|---|---|---|
| 1-89 | Me | H | o-MeOBoz | HO | Me | $CH_2$ | 1 |
| 1-90 | Me | H | HO | Ac | H | $CH_2$ | 1 |
| 1-91 | Me | H | HO | Ac | H | CO | 1 |
| 1-92 | Me | H | HO | Boz | H | $CH_2$ | 1 |
| 1-93 | Me | H | AcO | Ac | H | $CH_2$ | 1 |
| 1-94 | Me | H | BozO | Ac | H | $CH_2$ | 1 |
| 1-95 | Me | H | HOOCCH$_2$O— | Ac | H | $CH_2$ | 1 |
| 1-96 | Me | H | HOOC(CH$_2$)$_3$O— | Ac | H | $CH_2$ | 1 |
| 1-97 | Me | H | HOOCC(Me)$_2$O— | Ac | H | $CH_2$ | 1 |
| 1-98 | Me | Me | tBuOOCC(Me)$_2$O— | Me | Me | $CH_2$ | 1 |

TABLE 2

| Cpd. No. | $R^1$ | $R^2$ | $R^3$ | $R^4$ | $R^5$ | V |
|---|---|---|---|---|---|---|
| 2-1 | H | H | H | H | H | H |
| 2-2 | Me | H | H | H | H | H |
| 2-3 | Me | Me | Me | Me | Me | H |
| 2-4 | Me | H | Cl | H | H | H |
| 2-5 | Me | Me | HO | Me | Me | H |
| 2-6 | Me | Me | HO | Me | Me | Ac |
| 2-7 | Me | Me | HO | Me | Me | Va |
| 2-8 | Me | H | HO | tBu | H | Boz |
| 2-9 | Me | Me | AcO | Me | Me | Me |
| 2-10 | Me | Me | PrO | Me | Me | Pr |
| 2-11 | Me | Me | HO | Me | Me | HOOCCH$_2$— |
| 2-12 | Me | Me | HO | Me | Me | MeOOCCH$_2$— |
| 2-13 | Et | H | BozO | Me | Me | MeOOCCH$_2$— |
| 2-14 | Me | Me | HO | Me | Me | EtOOCCH$_2$— |
| 2-15 | Me | Me | HO | Me | Me | tBuOOCCH$_2$— |
| 2-16 | Me | Me | HO | Me | Me | HOOC(CH$_2$)$_3$— |
| 2-17 | Bu | H | MeO | Tmb | H | MeOOC(CH$_2$)$_3$— |
| 2-18 | Me | Me | HO | Me | Me | EtOOC(CH$_2$)$_3$— |
| 2-19 | Me | Me | HO | Me | H | tBuOOC(CH$_2$)$_3$— |
| 2-20 | Me | Me | HOOCCH$_2$O— | Me | Me | HOOC(CH$_2$)$_3$— |
| 2-21 | Me | Me | HOOC(CH$_2$)$_3$O— | Me | Me | HOOC(CH$_2$)$_3$— |
| 2-22 | Me | Me | HOOCC(Me)$_2$O— | Me | Me | HOOCC(Me)$_2$— |
| 2-23 | Me | H | H | HO | Me | H |
| 2-24 | Me | H | H | AcO | Me | Ac |
| 2-25 | Me | H | H | BozO | Me | Boz |
| 2-26 | Me | H | H | HOOCCH$_2$O— | Me | HOOCCH$_2$— |
| 2-27 | Me | H | H | EtOOCCH$_2$O— | Me | EtOOCCH$_2$— |
| 2-28 | Me | H | H | HOOC(CH$_2$)$_3$O— | Me | HOOC(CH$_2$)$_3$— |
| 2-29 | Me | H | H | MeOOC(CH$_2$)$_3$O— | Me | MeOOC(CH$_2$)$_3$— |
| 2-30 | Me | H | H | HOOCC(Me)$_2$O— | Me | HOOCC(Me)$_2$— |
| 2-31 | Me | H | H | tBuOOCC(Me)$_2$O— | Me | tBuOOCC(Me)$_2$— |

Of the compounds listed above, the following are particularly preferred, that is to say Compounds No. 1-2, 1-4, 1-7, 1-8, 1-9, 1-11, 1-12, 1-27, 1-30, 1-32, 1-33, 1-36, 1-37, 1-41, 1-45, 1-48, 1-52, 1-56, 1-61, 1-62, 1-70, 1-76 and 2-5. Compounds No.:

1-2. 5-[4-(2-Methylchroman-2-methoxy)benzylidene]-2,4thiazolidinedione;

1-7. 5-[4-(2,5,7-Trimethylchroman-2-methoxy)benzylidene]-2,4-thiazolidinedione;

1-8. 5-[4-(2,5,6,7,8-Pentamethylchroman-2-methoxy)benzylidene]-2,4-thiazolidinedione;

1-9. 5-[4-(7-Hydroxy-2,8-dimethylchroman-2-methoxy)benzylidene]-2,4-thiazolidinedione;

1-27. 5-[4-(6-Hydroxy-2,5,7,8-tetramethylchroman-2-methoxy)benzylidene]-2,4-thiazolidinedione;

1-37. 5-[4-(6-Acetoxy-2,5,7,8-tetramethylchroman-2-methoxy)benzylidene]-2,4-thiazolidinedione;

1-41. 5-[4-(6-Benzyloxy-2,5,7,8-tetramethylchroman-2-methoxy)benzylidene]-2,4-thiazolidinedione;

1-45. 5-[4-(6-Carboxymethoxy-2,5,7,8-tetramethylchroman-2-methoxy)benzylidene]-2,4-thiazolidinedione;

1-48. 5-{4-[6-(3-Carboxypropoxy)-2,5,7,8-tetramethylchroman-2-methoxy]benzylidene}-2,4-thiazolidinedione;

1-52. 5-{4-[6-(1-Carboxy-1-methylethoxy)-2,5,7,8-tetramethylchroman-2-methoxy]benzylidene}-2,4-thiazolidinedione;

1-56. 5-[4-(6-Carbamoylmethoxy-2,5,7,8-tetramethylchroman-2-methoxy)benzylidene]-2,4-thiazolidinedione;

1-61. 5-{4-[6-(Piperidinocarbonyl)methoxy-2,5,7,8-tetramethylchroman-2-methoxy]benzylidene}-2,4-thiazolidinedione;

1-62. 5-{4-[6-(Morpholinocarbonyl)methoxy-2,5,7,8-tetramethylchroman-2-methoxy]benzylidene}-2,4-thiazolidinedione; and 1-70. 5-[4-(6-Carboxy-2-methylchroman-2-methoxy)benzylidene]-2,4-thiazolidinedione;

being more preferred.

The most preferred compounds are Compounds No. 1-27, 1-37 and 1-41.

The benzylidenethiazolidine compounds of the present invention can be prepared by a variety of methods well known in the art for the preparation of compounds of this type. Thus, in general terms, the compounds of formula (I) may be prepared by reacting a compound of formula (II):

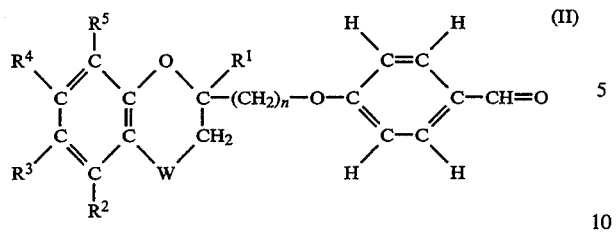
(II)

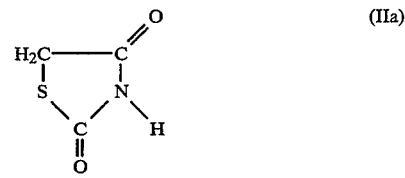
(IIa)

in which $R^1$, $R^2$, $R^3$, $R^4$, $R^5$, $\underline{n}$ and W are as defined above) with thiazolidine-2,4-dione, which may be represented by the formula (IIa):

The compound of formula (II), in turn, may be prepared by a variety of methods, and the overall sequence of reactions employed in the preparation of the compounds of the present invention may be illustrated by the following reaction scheme:

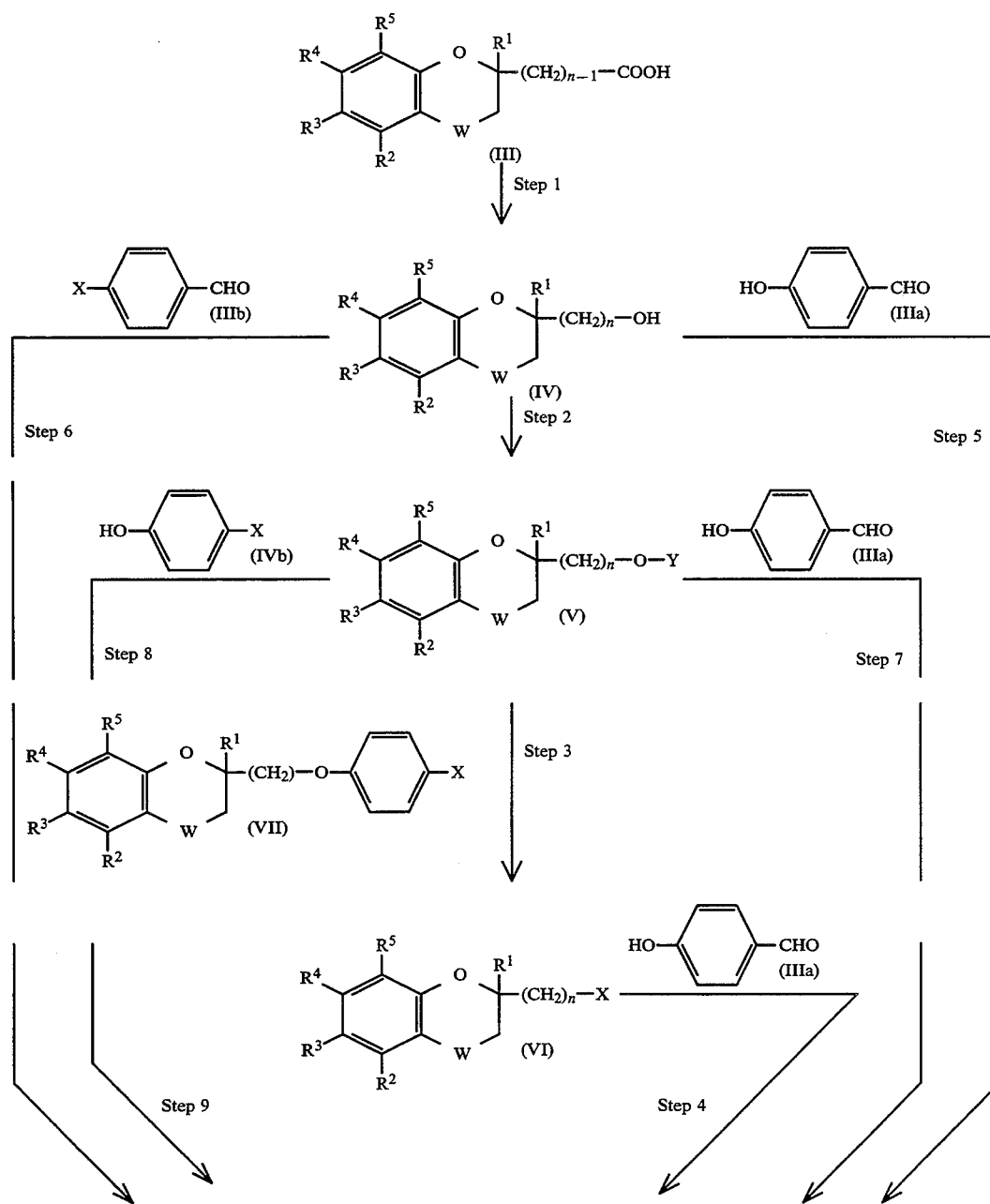

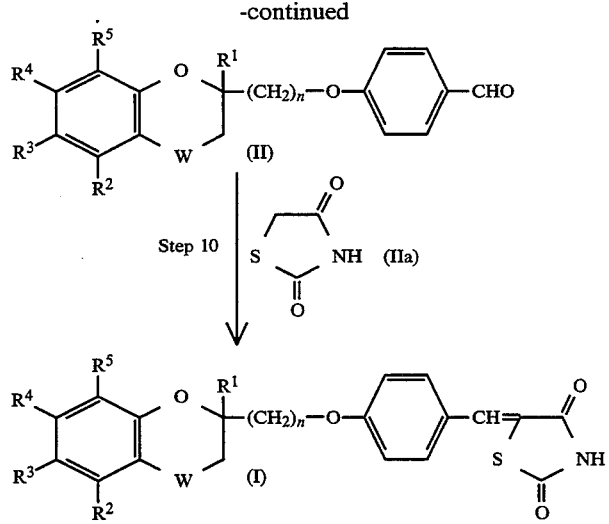

In the above formulae, R1, R2 R3, R4, R5, W and n are as defined above; X represents a halogen atom; and Y represents an alkylsulfonyl or arylsulfonyl group, as further defined and exemplified hereafter.

In Step 1 of the above reaction scheme, a compound of formula (IV) is prepared by reducing a compound of formula (III) [which may have been prepared, for example, as described in the Journal of the American Oil Chemists' Society, 51, 200 (1974); or Japanese Patent Provisional Publication Tokkai No. Sho 60-51189] using a suitable procedure, for example as described in Japanese Patent Provisional Publication Tokkai No. Sho 60-51189. In this procedure, the reduction is effected using a reducing agent such as lithium aluminum hydride or sodium bis[2-methoxyethoxy]aluminum hydride (trade name: Vitride). The reaction is preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran and ethylene glycol dimethyl ether; aromatic hydrocarbons, such as benzene, toluene and xylene; aliphatic hydrocarbons, such as hexane, heptane, cyclohexane, petroleum ether, ligroin and ethylcyclohexane. There is no particular limitation upon the amount of reducing agent employed, but a slight excess of the reducing agent over the amount of the compound of formula (III) is preferred. It is more preferred to use from 1 to 2 moles of the reducing agent per mole of the compound of formula (III). The reaction can take place over a wide range of temperatures, and the precise reaction temperature is not critical to the invention. In general, we find it convenient to carry out the reaction at a temperature of from 10° C. to 120° C. The time required for the reaction may also vary widely, depending on many factors, notably the reaction temperature and the nature of the reagents and solvents employed. However, provided that the reaction is effected under the preferred conditions outlined above, a period of from 10 minutes to 10 or more hours will usually suffice.

In Step 2 of the above reaction scheme, a compound of formula (V) is prepared by sulfonylation of the compound of formula (IV). This may be carried out by known techniques, for example as described in Japanese Patent Provisional Publication Tokkai No. Sho 63-139182. Thus, the compound of formula (IV) is subjected to sulfonylation, for example using a sulfonyl halide of formula Y-X, where Y represents an alkylsulfonyl group in which the alkyl part has from 1 to 5 carbon atoms (e.g. a methylsulfonyl, ethylsulfonyl, propylsulfonyl, butylsulfonyl or pentylsulfonyl group) or an arylsulfonyl group in which the aryl part is as defined and exemplified above in relation to the aryl groups included within substituents (b) (especially a phenyl group or a p-tolyl group), and X represents a halogen atom (e.g. a chlorine, fluorine, bromine or iodine atom). Examples of such sulfonylating agents include: alkylsulfonyl halides, such as methylsulfonyl chloride, ethylsulfonyl chloride and propylsulfonyl bromide; and arylsulfonyl halides, such as phenylsulfonyl chloride, p-tolylsulfonyl chloride and p-tolylsulfonyl bromide. The reaction is preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated aliphatic hydrocarbons, such as methylene chloride, 1,2-dichloroethane, chloroform and carbon tetrachloride; ethers, such as diethyl ether, dibutyl ether, diisobutyl ether, dioxane, tetrahydrofuran and ethylene glycol dimethyl ether; aromatic hydrocarbons, such as benzene, toluene and xylene; water; esters, such as ethyl acetate; amides, especially fatty acid amides, such as dimethylformamide; and mixtures of any two or more of these solvents. The reaction is normally and preferably carried out in the presence of an inorganic base, such as an alkali metal hydroxide (e.g. sodium hydroxide or potassium hydroxide) or an alkali metal carbonate (e.g. potassium carbonate or sodium carbonate); or an organic base, such as an alkylamine (e.g. triethylamine) or a heterocyclic amine (e.g. morpholine, N-ethylpiperidine or pyridine). There is no particular limitation on the ratio of the sulfonyl halide to the compound of formula (IV), but a slight excess of sulfonyl halide is preferred. It is more preferred to use from 1 to 2 moles, most preferably from 1.0 to 1.5 moles, of the sulfonyl halide per mole of the compound of formula (IV). The reaction will take place over a wide range of temperatures, and the precise reaction temperature chosen is not critical to the invention. In general, we find it convenient to carry out the reaction at a temperature in the range of from 10° to 100° C., more preferably from 10° to 50° C. The time required for the reaction may likewise vary widely, depending on many factors, notably the reaction temperature and the nature of the reagents. However, in most cases, a period of from a few hours to 10 or more hours will normally suffice.

In Step 3 of the above reaction scheme, a compound of formula (VI) is prepared by reacting the compound of formula (V) prepared in Step 2 with an alkali metal halide. Examples of alkali metal halides which may be used in this reaction include sodium iodide, sodium bromide and potassium iodide. The reaction is preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated aliphatic hydrocarbons, such as methylene chloride, 1,2-dichloroethane, chloroform and carbon tetrachloride; ethers, such as diethyl ether, dibutyl ether, diisobutyl ether, dioxane, tetrahydrofuran and ethylene glycol dimethyl ether; aromatic hydrocarbons, such as benzene, toluene and xylene; and amides, especially fatty acid amides, such as dimethylformamide. The reaction is preferably carried out by reacting the compound of formula (V) with sodium iodide in the presence of dimethylformamide. There is no particular limitation upon the ratio of the alkali metal halide to the compound of formula (V), but the reaction is most preferably carried out using from 5 to 30 moles, more preferably from 10 to 20 moles, of the alkali metal halide per mole of the compound of formula (V). The reaction will take place over a wide range of temperatures, and the precise reaction temperature chosen is not critical to the invention. In general, we find it convenient to carry out the reaction at a temperature in the range of from 100° to 200° C., more preferably from 130° to 180° C. The time required for the reaction may likewise vary widely, depending on many factors, notably the reaction temperature and the nature of the reagents and solvent employed. However, in most cases, a period of from a few hours to 10 or more hours will normally suffice.

In Step 4 of the above reaction scheme, a compound of formula (II) is prepared by reacting the compound of formula (VI) prepared as described in Step 3 with p-hydroxybenzaldehyde, which has the formula (IIIa), for example as described in Japanese Patent Provisional Publication Tokkai No. Sho 63-139182. The reaction is preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated aliphatic hydrocarbons, such as methylene chloride, 1,2-dichloroethane, chloroform and carbon tetrachloride; ethers, such as diethyl ether, dibutyl ether, diisobutyl ether, dioxane, tetrahydrofuran and ethylene glycol dimethyl ether; aromatic hydrocarbons, such as benzene, toluene and xylene; water; esters, such as ethyl acetate; amides, especially fatty acid amides, such as dimethylformamide; and mixtures of any two or more of these solvents. The reaction is normally and preferably carried out in the presence of a base, which may be: an inorganic base, such as an alkali metal hydroxide (e.g. sodium hydroxide or potassium hydroxide), an alkali metal carbonate (e.g. potassium carbonate or sodium carbonate) or an alkali metal halide (e.g. sodium iodide, sodium bromide or potassium bromide); or an organic base, such as an alkylamine (e.g. triethylamine); or a heterocyclic amine (e.g. morpholine, N-ethylpiperidine or pyridine). There is no particular limitation on the ratio of the p-hydroxybenzaldehyde to the compound of formula (VI), but the reaction is normally and preferably carried out using from 1 to 3 moles, more preferably from 1.5 to 2.5 moles, of p-hydroxybenzaldehyde per mole of the compound of formula (VI). The base is normally and preferably used in an amount of from 1 to 3 moles, more preferably from 1.5 to 2.5 moles, per mole of the compound of formula (VI). The reaction will take place over a wide range of temperatures, and the precise reaction temperature chosen is not critical to the invention. In general, we find it convenient to carry out the reaction at a temperature in the range of from 50° to 200° C., more preferably from 130° to 180° C. The time required for the reaction may likewise vary widely, depending on many factors, notably the reaction temperature and the nature of the reagents and solvent employed. However, in most cases, a period of from a few hours to 10 or more hours will normally suffice.

Step 5 of this reaction scheme provides an alternative to Steps 2 to 4. In Step 5, a compound of formula (II) is prepared directly from the compound of formula (IV) and p-hydroxybenzaldehyde of formula (IIIa) by a coupling reaction, for example as described in Japanese Patent Provisional Publication Tokkai No. Hei 1-131169. Examples of coupling agents which may be employed in this reaction include diethyl azodicarboxylate or triphenylphosphine. The reaction preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated aliphatic hydrocarbons, such as methylene chloride, 1,2-dichloroethane, chloroform or carbon tetrachloride; ethers, such as diethyl ether, dibutyl ether, diisobutyl ether, dioxane, tetrahydrofuran or ethylene glycol dimethyl ether; aromatic hydrocarbons, such as benzene, toluene or xylene; esters, such as ethyl acetate; amides, especially fatty acid amides, such as dimethylformamide; and mixtures of any two or more of these solvents. There is no particular limitation on the ratio of the compound of formula (IV) to the coupling agent, e.g. diethyl azodicarboxylate or triphenylphosphine, but it is preferred to use a slight molar excess of the coupling agent. We prefer to use from 1 to 2 moles, more preferably from 1.0 to 1.5 moles, of the coupling agent per mole of the compound of formula (IV). The reaction can take place over a wide range of temperatures, and the precise reaction temperature is not critical to the invention. In general, we find it convenient to carry out the reaction at a temperature of from 0° to 70° C. The time required for the reaction may also vary widely, depending on many factors, notably the reaction temperature and the nature of the reagents. However, provided that the reaction is effected under the preferred conditions outlined above, a period of from a few minutes to 10 or more hours will usually suffice.

Step 6 of this reaction scheme provides a further alternative to Steps 2 to 4. In Step 6, a compound of formula (II) is prepared by reacting the compound of formula (IV), prepared as described in Step 1, with a p-halobenzaldehyde of formula (IIIb) (particularly p-fluorobenzaldehyde), which reaction may, for example, be carried out as described in Japanese Patent Provisional Publication Tokkai No. Hei 1-131169. The reaction is preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated aliphatic hydrocarbons, such as methylene chloride, 1,2-dichloroethane, chloroform or carbon tetrachloride; ethers, such as diethyl ether, dibutyl ether, diisobutyl ether, dioxane, tetrahydrofuran or ethylene glycol dimethyl ether; aromatic hydrocarbons, such as benzene, toluene or xylene; amides, such as dimethylformamide; sulfoxides, such as dimethyl sulfoxide; and sulfones, such as sulfolane. In general, the reaction is preferably carried out in the presence of a base, which is preferably an essentially inorganic base, such as an alkali metal carbonate (e.g. potassium carbonate or sodium carbonate), an alkali metal hydride (e.g. sodium hydride); an alkali metal acetate (e.g. potassium acetate or sodium acetate); or an alkali metal alkoxide (e.g. sodium methoxide or sodium ethoxide). There is no particular limitation on the ratio of the p-halobenzaldehyde to the compound of formula (IV), but it is preferred to use a slight molar excess of the p-halobenzaldehyde to the compound of formula (Iv). In general, we prefer to use from 1 to 2 moles, more preferably from 1.0 to 1.5 moles, of the p-halobenzaldehyde per mole of the compound of formula (IV). The reaction can take place over a wide range of temperatures, and the precise reaction temperature is not critical to the invention. In general, we find it convenient to carry out the reaction at a temperature of from 100° to 170° C. The time required for the reaction may also vary widely, depending on many factors, notably the reaction temperature and the nature of the reagents and solvents employed. However, provided that the reaction is effected under the preferred conditions outlined above, a period of from a few minutes to 10 or more hours will usually suffice.

Step 7 of this reaction scheme provides an alternative to Steps 3 and 4. In Step 7, a compound of formula (V), prepared as described in Step 2, is reacted with p-hydroxybenzaldehyde of formula (IIIa), for example by the procedure described in Japanese Patent Provisional Publication Tokkai No. Sho 63-139182 to give a compound of formula (II). The reaction is essentially the same as that described in Step 4, and may be carried out in a similar manner to the procedure described in Step 4.

Steps 8 and 9 provide a further alternative to Steps 3 and 4.

In Step 8, a compound of formula (V), prepared as described in Step 2, is reacted with a p-halophenol of formula (IVb) to give a compound of formula (VII). The reaction is preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated aliphatic hydrocarbons, such as methylene chloride, 1,2-dichloroethane, chloroform and carbon tetrachloride; ethers, such as diethyl ether, dibutyl ether, diisobutyl ether, dioxane, tetrahydrofuran and ethylene glycol dimethyl ether; aromatic hydrocarbons, such as benzene, toluene and xylene; water; esters, such as ethyl acetate; amides, especially fatty acid amides, such as dimethylformamide; and mixtures of any two or more of these solvents. The reaction is normally and preferably carried out in the presence of a base, which may be: an inorganic base, such as an alkali metal hydroxide (e.g. sodium hydroxide or potassium hydroxide) or an alkali metal carbonate (e.g. potassium carbonate or sodium carbonate); or an organic base, such as an alkylamine (e.g. triethylamine) or a heterocyclic amine (e.g. morpholine, N-ethylpiperidine or pyridine). There is no particular limitation on the ratio of the p-halophenol of formula (IVb) to the compound of formula (V), but it is preferred to use a slight excess of the p-halophenol over the compound of formula (V). More preferably the reaction is carried out using from 1 to 2 moles, most preferably from 1.0 to 1.5 moles, of the p-halophenol per mole of the compound of formula (V). The reaction can take place over a wide range of temperatures, and the precise reaction temperature is not critical to the invention. In general, we find it convenient to carry out the reaction at a temperature of from 10 to 50° C., more preferably from 15° to 30° C. The time required for the reaction may also vary widely, depending on many factors, notably the reaction temperature and the nature of the reagents and solvents employed. However, provided that the reaction is effected under the preferred conditions outlined above, a period of from a few hours to 10 or more hours will usually suffice.

In Step 9 of this reaction scheme, the compound of formula (II) is prepared by reacting the compound of general formula (VII), prepared as described in Step 8, with butyllithium and dimethylformamide, for example as described in Japanese Patent Provisional Publication Tokkai No. Hei 1-186884. The reaction is preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, dibutyl ether, diisobutyl ether, dioxane, tetrahydrofuran and ethylene glycol dimethyl ether; and aromatic hydrocarbons, such as benzene, toluene and xylene. There is no particular limitation on the relative molar ratios of the compound of formula (VII), butyllithium and dimethylformamide, but, in general, the reaction is preferably carried out using about one mole of butyllithium and about one mole of dimethylformamide per mole of the compound of formula (VII). The reaction can take place over a wide range of temperatures, and the precise reaction temperature is not critical to the invention. In general, we find it convenient to carry out the reaction at a temperature of from $-70°$ to $-80°$ C., more preferably about $-80°$ C. The time required for the reaction may also vary widely, depending on many factors, notably the reaction temperature and the nature of the reagents and solvent employed. However, provided that the reaction is effected under the preferred conditions outlined above, a period of from a few hours to 10 or more hours will usually suffice.

In Step 10, the desired compound of formula (I) is prepared by reacting the compound of formula (II), which may have been prepared by any of the routes outlined above, with 2,4-thiazolidinedione, for example according to the procedure described in Japanese Patent Provisional Publication Tokkai No. Sho 63-139182. The reaction is preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol, propanol, butanol or ethylene glycol monomethyl ether; amides, especially fatty acid amides, such as dimethylformamide; sulfoxides, such as dimethyl sulfoxide; sulfones, such as sulfolane; ethers, such as dioxane, ethylene glycol dimethyl ether and tetrahydrofuran; ketones, such as acetone; nitriles, such as acetonitrile; organic acids, such as acetic acid; water; and mixtures of any two or more of these solvents. The reaction is normally and preferably carried out in the presence of a base, which may be: an inorganic base, such as an alkali metal carbonate (e.g. potassium carbonate or sodium carbonate), an alkali metal hydride (e.g. sodium hydride), an alkali metal acetate (e.g. potassium acetate or sodium acetate), an alkali metal alkoxide (e.g. sodium methoxide or sodium ethoxide) or ammonia; or an organic base, such as an alkylamine (e.g. methylamine, ethylamine, diethylamine or triethylamine); or a heterocyclic amine (e.g. morpholine, pyrrolidine, piperidine, $\underline{N}$-ethylpiperidine, piperazine or pyridine). There is no particular limitation on the ratio of the compound of formula (II) to the 2,4-thiazolidinedione, but the reaction is preferably carried out using from 1 to 4 moles, more preferably from 1 to 2.5 moles, of the 2,4-thiazolidinedione per mole of the compound of formula (II) and from 0.05 to 1 mole, more preferably from 0.2 to 0.6 mole, of the base per mole of the compound o#formula (II). The reaction can take place over a wide range of temperatures, and the precise reaction temperature is not critical to the invention. In general, we find it convenient to carry out the reaction at a temperature of from 40° C. to the reflux temperature of the reaction mixture, more preferably from 80° to 150° C. The time required for the reaction may also vary widely, depending on many factors, notably the reaction temperature and the nature of the reagents. However, provided that the reaction is effected under the preferred conditions outlined above, a period of from several tens of minutes to several tens of hours will usually suffice.

Alternatively, the compound of formula (I) may also be prepared by reacting 5-(4-hydroxybenzylidene)-2,4-thiazolidinedione [which may have been prepared, for example, as described in J. Med. Chem., 14, 528 (1971) or "Nippon Kagaku Zasshi" (the Journal of the Chemical Society of Japan), 92, 867 (1971)] with the compound of formula (VI), prepared as described in Step 3, or with the compound of formula (V), prepared as described in Step 2. In carrying out this alternative process, the reaction may be carried out in a similar manner and using similar reaction conditions to those described in Step 4 or Step 7, respectively.

In the compounds of formulae (I) through (VII), where $R^3$ and/or $R^4$ represents a hydroxy group, $R^3$ and/or $R^4$ can, if desired, be transformed to an alkylcarbonyloxy group, an arylcarbonyloxy group (which may optionally have one or more substituents on the aromatic ring) or an alkoxy group (which may optionally have one or more substituents), all as defined above for $R^3$ and/or $R^4$, by using the reactions described in the following optional steps. These reactions can be carried out, for example, as described in Japanese Patent Provisional Publication Tokkai No. Sho 62-5980.

Thus, compounds of formulae (I) through (VII) where $R^3$ and/or $R^4$ represents an alkylcarbonyloxy group or an arylcarbonyloxy group (whose aryl moiety may optionally have one or more substituents) can be prepared by contacting the corresponding compounds wherein $R^3$ and/or $R^4$ represents a hydroxy group with an acylating agent, which may be an alkylcarboxylic or arylcarboxylic acid, or an acid halide or acid anhydride thereof, corresponding to the carbonyloxy group which it is desired to introduce. The reaction is preferably effected in the presence of a dehydrating agent or catalyst, such as an inorganic acid (e.g. hydrochloric acid or sulfuric acid) or an organic acid (e.g. -toluenesulfonic acid). The reaction is normally carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran and dioxane; aromatic hydrocarbons, such as benzene, toluene and xylene; aliphatic hydrocarbons, such as hexane, cyclohexane and heptane; halogenated hydrocarbons, especially halogenated aliphatic hydrocarbons, such as methylene chloride and chloroform; ketones, such as acetone and methyl ethyl ketone; amides, especially fatty acid amides, such as dimethylformamide; sulfoxides, such as dimethyl sulfoxide; sulfones, such as sulfolane; organic bases, such as pyridine and triethylamine; water; and mixtures of any two or more of these solvents. There is no particular limitation on the ratio of the starting compound and the acylating agent, but the reaction is preferably carried out using a slight molar excess of the acylating agent, more preferably from 1 to 10 moles of the acylating agent per mole of the starting compound. The reaction can take place over a wide range of temperatures, and the precise reaction temperature is not critical to the invention. In general, we find it convenient to carry out the reaction at a temperature of from 0° to 100° C. The time required for the reaction may also vary widely, depending on many factors, notably the reaction temperature and the nature of the reagents and solvent employed. However, provided that the reaction is effected under the preferred conditions outlined above, a period of from several minutes to 10 or more hours will usually suffice.

Those compounds of formulae (I) through (VII) where $R^3$ and/or $R^4$ represents an alkoxy group (which may optionally have one or more substituents) may be prepared by contacting the corresponding compounds wherein $R^3$ and/or $R^4$ represents a hydroxy group with an alkyl halide (preferably bromide) which may have one or more substituents, preferably in the presence of a base. The reaction is normally carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran or dioxane; aromatic hydrocarbons, such as benzene, toluene and xylene; aliphatic hydrocarbons such as hexane, cyclohexane and heptane; halogenated hydrocarbons, especially halogenated aliphatic hydrocarbons, such as methylene chloride and chloroform; ketones, such as acetone and methyl ethyl ketone; amides, especially fatty acid amides, such as dimethylformamide; sulfoxides, such as dimethyl sulfoxide; sulfones, such as sulfolane; water; and mixtures of any two or more of these solvents. Examples of the bases which may be used in this reaction include: inorganic bases, such as an alkali metal carbonate (e.g. sodium carbonate or potassium carbonate), an alkali metal bicarbonate (e.g. sodium bicarbonate or potassium bicarbonate), an alkali metal hydroxide (e.g. sodium hydroxide or potassium hydroxide), an alkaline earth metal hydroxide (e.g. calcium hydroxide), an alkali metal hydride (e.g. sodium hydride or potassium hydride), an alkali metal alkoxides (e.g. sodium methoxide, sodium ethoxide or potassium t-butoxide), an organic lithium compound (e.g. butyllithium or t-butyllithium), a lithium dialkylamide (e.g. lithium diisopropylamide or lithium dicyclohexylamide) or ammonia; and organic bases, such as an alkylamine (e.g. methylamine, ethylamine, diethylamine or triethylamine) or a heterocyclic amine (e.g. morpholine, pyrrolidine, piperidine, N-ethylpiperidine, piperazine or pyridine). The ratio of the alkyl halides to the starting compound is preferably from 1 to 10 moles of alkyl halide per mole of the starting compound, and the ratio of the base to the starting compound is preferably from 1 to 10 moles of the base per mole of the starting compound. The reaction can take place over a wide range of temperatures, and the precise reaction temperature is not critical to the invention. In general, we find it convenient to carry out the reaction at a temperature from $-10°$ to $100°$ C. The time required for the reaction may also vary widely, depending on many factors, notably the reaction temperature and the nature of the reagents and solvent employed. However, provided that the reaction is effected under the preferred conditions outlined above, a period of from several minutes to several days will usually suffice.

Furthermore, those compounds where $R^3$ and/or $R^4$ represents an alkoxy group which is substituted by a substituted or unsubstituted carbamoyl group of formula —$CONR^6R^7$, can be prepared by amidation of the corresponding compound having a carboxy or alkoxycarbonyl group with ammonia or with an amine, by conventional means. Alternatively, a compound wherein $R^3$ and/or $R^4$ represents an alkoxy group substituted with a carbamoyl group can be prepared from the corresponding compound wherein $R^3$ and/or $R^4$ represents a hydroxy group by reaction of the compound wherein $R^3$ and/or $R^4$ represents a hydroxy group with a carbamoylalkyl halide in the presence of two equivalents of sodium hydride in dimethylformamide.

Conversely, those compounds of formulae (I) through (VII) where $R^3$ and/or $R^4$ represents an alkylcarbonyloxy group, an arylcarbonyloxy group (which may optionally have one or more substituents on the aromatic ring) or an alkoxy group (which may optionally have one or more substituents) can, if desired, be converted to the corresponding compounds where $R^3$ and/or $R^4$ represents a hydroxy group. The reaction can be carried out, for example, as described in Japanese Patent Provisional Publication Tokkai No. Sho 62-5980. This reaction is a conventional hydrolysis reaction and may be carried out using any reagent commonly used in the art for this type of reaction, for example: an inorganic acid such as hydrochloric acid, sulfuric acid or nitric acid; or an organic acid such as p-toluenesulfonic acid. The reaction is normally carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, propanol or butanol; ethers, such as diethyl ether, tetrahydrofuran or dioxane; aromatic hydrocarbons, such as benzene, toluene or xylene; aliphatic hydrocarbons, such as hexane, cyclohexane or heptane; halogenated hydrocarbons, especially halogenated aliphatic hydrocarbons, such as methylene chloride or chloroform; ketones, such as acetone or methyl ethyl ketone; amides, especially fatty acid amides, such as dimethylformamide; sulfoxides, such as dimethyl sulfoxide; sulfones, such as sulfolane; organic acids, such as acetic acid or propionic acid; water; and mixtures of any two or more of these solvents. Preferred solvents include water and organic acids, such as acetic acid. The amount of acid used is preferably from 0.001 to 5 moles, more preferably from 0.01 to 1 mole, per mole of the starting compound. The reaction can take place over a wide range of temperatures, and the precise reaction temperature not critical to the invention. In general, we find it convenient to carry out the reaction at a temperature of from room temperature to $100°$ C. The time required for the reaction may also vary widely, depending on many factors, notably the reaction temperature and the nature of the reagents and solvent employed. However, provided that the reaction is effected under the preferred conditions outlined above, a period of from several minutes to 10 or more hours will usually suffice.

Similarly, where W represents a group of formula C=N—OV (wherein V represents a hydrogen atom, an alkylcarbonyl group, an arylcarbonyl group or an alkyl group which may optionally have one or more substituents), any group or atom represented by V can be converted to any other group or atom so represented by a similar reaction to those described above in relation to the groups represented by $R^3$ and $R^4$.

Thus, when V represents a hydrogen atom, it can be converted to an alkylcarbonyl group, an arylcarbonyl group or an alkyl group which may optionally be substituted, and conversely when V represents an alkylcarbonyl group, an arylcarbonyl group or an alkyl group which may optionally be substituted, it can be converted to a hydrogen atom by hydrolysis according to the procedure described above.

Furthermore, in the compounds of formulae (I) through (VII), where $R^3$ and/or $R^4$ represents a formyl group, an alkylcarbonyl group, an arylcarbonyl group (which may optionally have one or more substituents on the aromatic ring), a carboxy group, an alkoxycarbonyl group, an aryloxycarbonyl group or a halogen atom, these compounds can be converted into each other, if necessary, by any appropriate combination of oxidation, reduction, halogenation, hydrolysis or neutralization according to conventional means.

After completion of any or all of the above reactions, the desired compounds obtained in any reaction can be separated from the reaction mixture and then purified, if necessary, by conventional means, for example the various chromatography techniques, notably column chromatography, recrystallization or reprecipitation. For example, in one suitable recovery procedure, the reaction mixture is mixed with a solvent and extracted with that solvent; the mixture is then freed from the solvent by distillation. The resulting residue may be purified by column chromatography through silica gel to yield the desired compound as a pure specimen.

If required, the resolution of isomers can be carried out by conventional resolution and purification techniques at any appropriate time.

The benzylidenethiazolidine compounds of formula (I) according to the present invention are useful as intermediates for preparing the corresponding benzylthiazolidine compounds (for example, see Japanese Patent Provisional Publication Tokkai No. Sho 60-51189, No. Sho 62-5980, No. Sho 64-38090 and the like), i.e. compounds of formula (Ia):

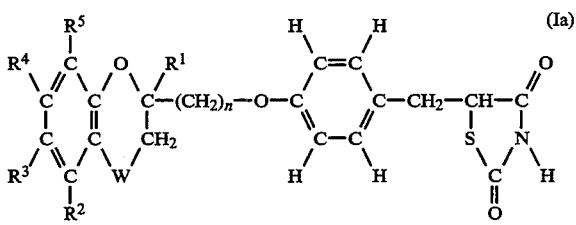

(in which R to R, W and $\underline{n}$ are as defined above) by reduction, and such a process also forms part of the present invention.

The preparation of the benzylthiazolidine derivatives from the benzylidenethiazolidine compounds of the present invention may be carried out by means of a conventional reduction of a double bond. The reaction may be carried out using any reducing agent known to be capable of reducing a double bond without adversely affecting other parts of the molecule.

For example, one suitable reduction reaction comprises contacting the benzylidenethiazolidine compound with hydrogen in the presence of a noble metal catalyst, which is preferably supported, such as platinum, palladium or rhodium, particularly palladium-on-charcoal. The reaction is normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: etherst such as diethyl ether, tetrahydrofuran or dioxane; alcohols, such as methanol, ethanol, isopropanol or butanol; aromatic hydrocarbons, such as benzene or toluene; amides, especially fatty acid amides, such as dimethylformamide or dimethylacetamide; carboxylic acids, such as formic acid, acetic acid or propionic acid; water; and mixtures of any two or more thereof. Hydrogenation may be carried out under atmospheric pressure or, more preferably, under superatmospheric pressure in a closed pressure vessel. The amount of catalyst used is preferably from 0.01 to 25% by weight of the compound of formula (I). The reaction can take place over a wide range of temperatures, and the precise reaction temperature is not critical to the invention. In general, we find it convenient to carry out the reaction at a temperature of from 0° to 100° C. The time required for the reaction may also vary widely, depending on many factors, notably the reaction temperature and the nature of the reagents and solvent employed. However, provided that the reaction is effected under the preferred conditions outlined above, a period of from several minutes to 10 or more hours will usually suffice.

An alternative reduction reaction comprises contacting the benzylidenethiazolidine compound with a metal amalgam, such as sodium amalgam or aluminum amalgam, particularly sodium amalgam. The reaction is effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol. The reaction can take place over a wide range of temperatures, and the precise reaction temperature is not critical to the invention. In general, we find it convenient to carry out the reaction at about room temperature. The time required for the reaction may also vary widely, depending on many factors, notably the reaction temperature and the nature of the reagents and solvent employed. However, provided that the reaction is effected under the preferred conditions outlined above, a period of from several minutes to 10 or more hours will usually suffice.

A further alternative reduction method comprises treating the benzylidenethiazolidine compound with a metal, e.g. zinc, iron or tin in an acid, which may be an inorganic acid (e.g. hydrochloric acid, hydrobromic acid or sulfuric acid) or an organic acid (e.g. acetic acid). The reaction can take place over a wide range of temperatures, and the precise reaction temperature is not critical to the invention. In general, we find it convenient to carry out the reaction at the reflux temperature of the reaction mixture. The time required for the reaction may also vary widely, depending on many factors, notably the reaction temperature and the nature of the reagents. However, provided that the reaction is effected under the preferred conditions outlined above, a period of from several minutes to 10 or more hours will usually suffice.

After completion of the reaction, the desired benzylthiazolidine derivatives can be purified by said conventional means, such as column chromatography, recrystallization, reprecipitation and the like.

The compounds of the present invention exhibited the ability to inhibit the formation of lipid peroxide in the mammalian body in the test system described by Malvy et al. [Biochem. Biophys. Res. Commun., 95, 734 (1980)]. Accordingly, these compounds may be used for the treatment of human arteriosclerosis and complications thereof.

The compounds of the invention may be administered orally, for example in the form of tablets, syrups, capsules, powders or granules, or parenterally, for example by injection (intravenous, subcutaneous or intramuscular) or in the form of a suppository. Alternatively, they may be formulated for topical administration, e.g. to the eyes. For example, for administration to the eye mucosa, it is preferred that the compounds of the invention should be administered in the form of eye drops or eye ointments, the formulation of which is well known in the art. Depending upon the nature of the formulation, they may be used alone or in admixture with one or more conventional adjuvants. Examples include excipients, binders, disintegrating agents, lubricants, corrigents, solubilizing agents, suspension aids and coating agents.

The recommended dosage will, of course, vary depending upon the age and body weight of the patient as well as the nature and severity of the disease, and the intended route of administration. However, for an adult human patient, a daily dose of from 5.0 mg to 2000 mg (which may be administered in a single dose or in divided doses) is recommended in the treatment of hyperlipaemia, diabetes mellitus and complications thereof, when administered orally or parenterally.

The invention is further illustrated by the following Examples, which show the preparation of certain of the compounds of the present invention, and by the subsequent Preparations, of which Preparations 1, 2 and 3 show the preparation of some of the starting materials used in these Examples and Preparations 4, 5 and 6 show the use of the compounds of the present invention in the preparation of their corresponding benzyl derivatives. In these Examples and Preparations, the Nuclear Magnetic Resonance Spectra were measured in the solvent specified in each case, scanning at either 60 MHz or 270 MHz, as specified, and using tetramethylsilane as the internal standard.

EXAMPLE 1

5-[4-(6-Benzyloxy-2,5,7,8-tetramethylchroman-2-methoxy)benzylidene]-2,4-thiazolidinedione (Compound No. 1-41)

4.7 g of 2,4-thiazolidinedione and 0.92 g of piperidine were added to a solution of 11.6 g of 6-benzyloxy-2-[(4-formylphenyl)oxymethyl]-2,5,7,8-tetramethylchroman (prepared as described in Preparation 3) dissolved in 60 ml of 2-methoxyethanol, and the resulting mixture was heated under reflux for 1.5 hours. At the end of this time, the reaction mixture was extracted with methylene chloride. The extract was washed with water, and then the solvent was removed by distillation under reduced pressure. The residue thus obtained was recrystallized from methanol, to afford 11.2 g of the title compound, melting at 190°–193° C. Nuclear Magnetic Resonance Spectrum (hexadeuterated dimethyl sulfoxide, 60 MHz), $\delta$ ppm: 1.33 (3H, singlet); 1.83–2.33 (2H, multiplet); 1.97 (3H, singlet); 2.10 (6H, singlet); 2.40–2.90 (2H, multiplet); 4.07 (2H, singlet); 4.63 (2H, singlet); 7.10 (2H, doublet, J=9 Hz); 7.40 (5H, singlet); 7.47 (2H, doublet, J=9 Hz); 7.73 (1H, singlet).

EXAMPLE 2

5-[4-(6-Acetoxy-2,5,7,8-tetramethylchroman-2-methoxy)benzylidene]-2,4-thiazolidinedione (Compound No. 1-37)

4.74 g of 2,4-thiazolidinedione and 0.92 g of piperidine were added to a solution of 10.3 g of 6-acetoxy-2-[(4-formylphenyl)oxymethyl]-2,5,7,8-tetramethylchroman (prepared by a procedure similar to that described in Preparations 1, 2 and 3) dissolved in 60 ml of 2-methoxyethanol, and the resulting mixture was heated under reflux for 1.5 hours. At the end of this time, the reaction mixture was treated in a similar manner to that described in Example 1, to afford 10.0 g of the title compound, melting at 203°–205.5° C.

Nuclear Magnetic Resonance Spectrum (hexadeuterated dimethyl sulfoxide, 60 MHz), $\delta$ ppm: 1.40 (3H, singlet); 1.80–2.17 (2H, multiplet); 1.97 (6H, singlet); 2.03 (3H, singlet); 2.30 (3H, singlet); 2.43–2.90 (2H, multiplet); 4.03 (2H, singlet); 7.00 (2H, doublet, J=9 Hz); 7.40 (2H, doublet, J=9 Hz); 7.67 (1H, singlet).

EXAMPLE 3

5-[(6-Hydroxy-2,5,7,8-tetramethylchroman-2-methoxy)benzylidene]-2,4-thiazolidinedione Compound No. 1-27)

15 ml of concentrated hydrochloric acid were added to a solution of 15.4 g of 5-[4-(6-benzyloxy-2,5,7,8-tetramethylchroman-2-methoxy)benzylidene]-2,4-thiazolidinedione (prepared as described in Example 1) dissolved in 60 ml of acetic acid, and the resulting mixture was heated under reflux for 1.5 hours. At the end of this time, the reaction mixture was mixed with 200 ml of ethyl acetate and 100 ml of water, and the pH was adjusted to a value of 7 by the addition of a 2N aqueous solution of sodium hydroxide. The ethyl acetate layer was separated and was washed with water to remove impurities, and the aqueous layer was extracted with ethyl acetate to separate the desired compound. After the same washing and extraction procedures had been repeated twice, the combined ethyl acetate extracts were concentrated by distillation under reduced pressure. The residue thus obtained was washed with methanol and 11.6 g of the title compound were collected by filtration.

Nuclear Magnetic Resonance Spectrum (hexadeuterated dimethyl sulfoxide, 60 MHz), $\delta$ ppm: 1.43 (3H, singlet); 2.10 (6H, singlet); 2.13 (3H, singlet); 2.20–2.43 (2H, multiplet); 2.47–2.90 (2H, multiplet); 3.70–5.53 (1H, broad); 4.03 (2H, singlet); 7.03 (2H, doublet, J=9 Hz); 7.50 (2H, doublet, J=9 Hz); 7.87 (1H, singlet).

EXAMPLE 4

5-[4-(6-Acetoxy-2,5,7,8-tetramethylchroman-2-methoxy)benzylidene]-2,4-thiazolidinedione (Compound No. 1-37)

0.71 g of acetic anhydride and 0.55 g of pyridine were added to a solution of 1.5 g of 5-[4-(6-hydroxy-2,5,7,8-tetramethylchroman-2-methoxy)benzylidene]2,4-thiazolidinedione (prepared as described in Example 3) dissolved in 7.5 ml of toluene, and the resulting mixture was stirred at room temperature for 5 hours. At the end of this time, the reaction mixture was washed with water, and the solvent was removed by distillation under reduced pressure. After trituration with methanol, the crystals thus obtained were collected by filtration to afford 1.2 g of the title compound.

The nuclear magnetic resonance spectrum of this compound was identical to that of the product of Example 2.

EXAMPLE 5

5-[4-(6-t-Butoxycarbonylmethoxy-2,5,7,8-tetramethylchroman-2-methoxy)benzylidene]-2,4-thiazolidinedione (Compound No. 1-98)

500 mg of 5-[4-(6-hydroxy-2,5,7,8-tetramethylchroman-2-methoxy)benzylidene]-2,4-thiazolidinedione (prepared as described in Example 3) were dissolved in 10 ml of dimethylformamide, and 220 mg of sodium hydride (as a 55% w/w dispersion in mineral oil) were added to the resulting solution, whilst ice-cooling. The resulting mixture was then stirred at room temperature for 40 minutes. At the end of this time, the mixture was again ice-cooled, and 240 mg of t-butyl bromoacetate were added dropwise to it; it was then stirred for 45 minutes, whilst ice-cooling. At the end of this time, the reaction mixture was poured into water and extracted with ethyl acetate. The extract was dried over anhydrous sodium sulfate and freed from the solvent by distillation under reduced pressure. The residue thus obtained was subjected to column chromatography through silica gel, using a 3 : 1 by volume mixture of hexane and ethyl acetate as the eluent, to afford 360 mg of the title compound as a pale yellow powder, softening at 103°–120° C.

Nuclear Magnetic Resonance Spectrum (CDCl$_3$, 270 MHz), δ ppm: 1.42 (3H, singlet); 1.53 (9H, singlet); 1.85–2.0 (1H, multiplet); 2.05 (3H, singlet); 2.05–2.2 (1H, multiplet); 2.15 (3H, singlet); 2.19 (3H, singlet); 2.62 (2H, broad triplet, J=6 Hz); 3.97 and 4.04 (2H, AB type, J=9 Hz); 4.17 (2H, singlet); 7.02 (2H, doublet, J=9 Hz); 7.44 (2H, doublet, J=9 Hz); 7.80 (1H, singlet); 8.06 (1H, broad singlet).

EXAMPLE 6

5-[4r(6-Carboxymethoxy-2,5,7,8-tetramethylchroman-2-methoxy)benzylidene]-2,4-thiazolidinedione (Compound No. 1-45)

A mixture of 350 mg of 5-[4-(6-t-butoxycarbonylmethoxy-2,5,7,8-tetramethylchroman-2-methoxy)benzylidene]-2,4-thiazolidinedione (prepared as described in Example 5) and 3 ml of a 4N solution of hydrogen chloride in dioxane was allowed to stand overnight at room temperature. At the end of this time, the reaction mixture was freed from the solvent by distillation under reduced pressure. The residue thus obtained was subjected to column chromatography through silica gel using a 3 : 1 : 0.5 by volume mixture of hexane, ethyl acetate and acetic acid as the eluent, to afford 180 mg of the title compound as a pale yellow powder, melting at 197°–199° C.

Nuclear Magnetic Resonance Spectrum (hexadeuterated dimethyl sulfoxide, 270 MHz), δ ppm: 1.32 (3H, singlet); 1.8–2.1 (2H, multiplet); 1.94 (3H, singlet); 2.08 (6H, singlet); 2.60 (2H, broad triplet, J=6 Hz); 4.07 and 4.11 (2H, AB type, J=10 Hz); 4.18 (2H, singlet); 7.14 (2H, doublet, J=9 Hz); 7.54 (2H, doublet, J=9 Hz); 7.75 (1H, singlet); 12.50 (1H, broad singlet).

EXAMPLE 7

5-{4-[6-(1-Ethoxycarbonyl-1-methylethoxy)-2,5,7,8-tetramethylchroman-2-methoxy]benzylidene}-2,4-thiazolidinedione (Compound No. 1-53)

Following the procedure described in Example 5, but using 300 mg of 5-[4-(6-hydroxy-2,5,7,8-tetramethylchroman-2-methoxy)benzylidene]-2,4-thiazolidinedione (prepared as described in Example 3) 150 mg of ethyl α-bromoisobutyrate, 70 mg of sodium hydride (as a 55% w/w dispersion in mineral oil) and 5 ml of dimethylformamide, 170 mg of the title compound, melting at 69°–72° C., were obtained.

Nuclear Magnetic Resonance Spectrum (CDCl$_3$, 270 MHz), δ ppm: 1.35 (3H, triplet, J=7 Hz); 1.41 (9H, singlet); 1.85–2.2 (2H, multiplet); 2.02 (3H, singlet); 2.06 (3H, singlet); 2.10 (3H, singlet); 2.60 (2H, broad triplet, J=6 Hz); 3.98 and 4.04 (2H, AB type, J=9 Hz); 4.27 (2H, quartet, J=7 Hz); 7.01 (2H, doublet, J=9 Hz); 7.44 (2H, doublet, J=9 Hz); 7.80 (1H singlet); 8.07 (1H, broad singlet).

EXAMPLE 8

5-{4-[6-(1-Carboxy-1-methylethoxy)-2,5,7,8-tetramethylchroman-2-methoxy]benzylidene}-2,4,-thiazolidinedione (Compound No. 1-52)

A mixture of 60 mg of 5-{4-[6-(1-ethoxycarbonyl-1-methylethoxy)-2,5,7,8-tetramethylchroman-2-methoxy]benzylidene}-2,4-thiazolidinedione (prepared as described in Example 7), 0.25 ml of a 2N aqueous solution of sodium hydroxide and 1 ml of methanol was allowed to stand at room temperature for 3 days. At the end of this time, the reaction mixture was acidified with dilute aqueous hydrochloric acid and extracted with ethyl acetate. The extract was dried over anhydrous sodium sulfate, and then the solvent was removed by distillation under reduced pressure, to afford 40 mg of the title compound as a pale yellow powder.

Nuclear Magnetic Resonance Spectrum (hexadeuterated dimethyl sulfoxide, 270 MHz), δ ppm: 1.29 (6H, singlet); 1.32 (3H, singlet); 1.8–2.1 (2H, multiplet); 1.92 (3H, singlet); 2.04 (6H, singlet); 2.59 (2H, broad triplet, J=6 Hz); 4.10 (2H, broad singlet); 7.13 (2H, doublet, J=9 Hz); 7.53 (2H, doublet, J=9 Hz); 7.75 (1H, singlet); 12.50 (1H, broad singlet).

PREPARATION 1

6-Benzyloxy-2,5,7,8-tetramethylchroman-2-methyl methanesulfonate 25.54 g of methanesulfonyl chloride were added dropwise, whilst ice-cooling, to a solution of 56.57 g of 6-benzyloxy-2,5,7,8-tetramethylchroman-2-methanol dissolved in 560 ml of methylene chloride, and the resulting mixture was heated under reflux for 1 hour. At the end of this time, the reaction mixture was washed with water, and the solvent was removed by distillation under reduced pressure. After the residue had been triturated with methanol, the crystals thus obtained were collected by filtration to afford 68.43 g of the title compound, melting at 90°–96° C.

Nuclear Magnetic Resonance Spectrum (CDCl$_3$, 60 MHz), δ ppm: 1.30 (3H, singlet); 1.70–2.03 (2H, multiplet); 2.10 (3H, singlet); 2.13 (3H, singlet); 2.20 (3H, singlet); 2.43–2.87 (2H, multiplet); 2.97 (3H, singlet); 4.17 (2H, singlet); 4.67 (2H, singlet); 7.10–7.63 (5H, multiplet).

PREPARATION 2

6-Benzyloxy-2-iodomethyl-.2,5,7,8,-tetramethylchroman 224.8 g of sodium iodide were added to a solution of 40.44 g of 6-benzyloxy-2,5,7,8-tetramethylchroman-2-methyl methanesulfonate (prepared as described in Preparation 1) dissolved in 600 ml of dimethylformamide, and the resulting mixture was heated under reflux for 4 hours. At the end of this time, the reaction mixture was extracted with 200 ml of hexane. The extract was washed with water, and the solvent was removed by distillation under reduced pressure. After the residue had been triturated with methanol, the crystals thus obtained were collected by filtration to afford 29.14 g of the title compound, melting at 95°–98° C.

Nuclear Magnetic Resonance Spectrum (CDCl$_3$, 60 MHz), δ ppm: 1.47 (3H, singlet); 1.80–2.10 (2H, multiplet); 2.13 (6H, singlet); 2.20 (3H, singlet); 2.33–2.80 (2H, multiplet); 3.30 (2H, singlet); 4.67 (2H, singlet); 7.17–7.63 (5H, multiplet).

PREPARATION 3

6-Benzyloxy-2-[(4-formylphenyl)oxymethyl]-2,5,7,8-tetramethylchroman

A mixture of 1.63 g of sodium hydride (as a 55% w/w dispersion in mineral oil) and 20 ml of dimethylformamide was cooled in an atmosphere of nitrogen; to the cooled solution were then added dropwise a mixture of 4.58 g of p-hydroxybenzaldehyde and 30 ml of dimethylformamide, whilst ice-cooling. 10.9 g of 6-benzyloxy-2-iodomethyl-2,5,7,8-tetramethylchroman (prepared as described in Preparation 2) and 50 ml of dimethylformamide were then added to the resulting solution, and the resulting mixture was heated under reflux for 5.5 hours. At the end of this time, the reaction mixture was extracted twice, each time with 100 ml of ethyl acetate. The combined extracts were washed with water, and the solvent was then removed from the extract by distillation under reduced pressure to afford 10.5 g of the title compound as an oil. Nuclear Magnetic Resonance Spectrum ($CDCl_3$, 60 MHz), δ ppm: 1.43 (3H, singlet); 1.63-2.27 (2H, multiplet); 2.03 (3H, singlet); 2.13 (3H, singlet); 2.20 (3H, singlet); 2.43-2.90 (2H, multiplet); 4.00 (2H, singlet); 4.63 (2H, singlet); 6.97 (2H, doublet, J=9 Hz); 7.10-7.60 (5H, multiplet); 7.77 (2H, doublet, J=9 Hz); 9.77 (1H, singlet).

PREPARATION 4

5-[4-(6-Hydroxy-2,5,7,8-tetramethylchroman-2-methoxy)-benzyl]-2,4-thiazolidinedione 1.5 g of 5-[4-(6-hydroxy-2,5,7,8-tetramethylchroman-2-methoxy)benzylidene]-2,4-thiazolidinedione (prepared as described in Example 3) was dissolved in a mixture of 200 ml of acetic acid and 3 ml of water and catalytically reduced at 60°-70° C. for 3 hours under a pressure of 4 kg/cm² of hydrogen in the presence of 1.5 g of 10% w/w palladium-on-charcoal. At the end of this time, 1.3 g of the title compound, melting at 184°-186° C., was obtained from the reaction mixture.

Nuclear Magnetic Resonance Spectrum (hexadeuterated acetone, 60 MHz), δ ppm: 1.39 (3H, singlet); about 2 (2H, multiplet); 2.02 (3H, singlet); 2.09 (3H, singlet); 2.13 (3H, singlet); 2.63 (2H, broad triplet, J=6 Hz); 3.07 (1H, doublet of doublets, J=15 & 9 Hz); 3.41 (1H, doublet of doublets, J=15 & 4.5 Hz); 3.97 (2H, J=9 Hz); 4.70 (1H, doublet of doublets, J=15 & 4.5 Hz); 6.90 (2H, doublet, J=9 Hz); 7.21 (2H, doublet, J=9Hz).

PREPARATION 5

5-[4-(6-Acetoxy-2,5,7,8-tetramethylchroman-2-methoxy)benzyl]2,4-thiazolidinedione 4.3 g of 5-[4-(6-acetoxy-2,5,7,8-tetramethylchroman-2-methoxy)benzylidene]-2,4-thiazolidinedione were dissolved in a mixture of 200 ml of acetic acid and 20 ml of water and catalytically reduced at 55°-70° C. under a pressure of 3 kg/cm of hydrogen for 2.5 hours in the presence of 4.3 g of 10% w/w palladium-on-charcoal. At the end of this time, the catalyst was removed by filtration from the reaction mixture. The solvent was removed from the filtrate by distillation under reduced pressure, and the residue thus obtained was mixed with 80 ml of ethyl acetate and 80 ml of water. The pH of the mixture was adjusted to a value of 7 by the addition of a 2N aqueous solution of sodium hydroxide. The ethyl acetate layer was extracted with 80 ml of water to remove impurities. The aqueous layer was then extracted with 80 ml of ethyl acetate to give the desired compound. The operation was repeated twice. The combined extracts were freed from the solvent by distillation under reduced pressure to afford 3.4 g of the title compound.

Nuclear Magnetic Resonance Spectrum ($CDCl_3$, 270 MHz), δ ppm: 3.03 (1H, doublet of doublets, J=15, 9 Hz); 3.42 (1H, doublet of doublets, J=15, 4.5 Hz); 4.45 (1H, doublet of doublets, J=9, 4.5 Hz).

PREPARATION 6

5-{4-[6-(1-Carboxy-1-methylethoxy)-2,5,7,8-tetramethylchroman-2-methoxy]benzyl}-2,4-thiazolidinedione Following a procedure similar to that described in Preparation 5, the title compound is synthesized by reduction of 5-{4-[6-(1-carboxy-1-methylethoxy)-2,5,7,8-tetramethylchroman-2-methoxy]benzylidene}-2,4-thiazolidinedione, prepared as described in Example 8.

The benzylthiazolidine compound prepared in Preparation 6 above is a known compound and is described in Japanese Patent Provisional Publication (Tokkai) No. Sho. 62-5980 (Example 79). This benzylthiazolidine compound is an excellent inhibitor of aldose reductase activity. Accordingly, the benzylidenethiazolidine compound employed as a starting material in this Preparation is useful as a synthetic intermediate for preparing the corresponding benzylthiazolidine compound.

BIOLOGICAL ACTIVITY

Inhibitory activity on the formation of lipid peroxide

This was investigated by the ferrous sulfate/cysteine method described by Malvy et al. [Biochem. Biophys. Res. Commun., 95, 734 (1980)]. The compound under test at various concentrations, cysteine (500 μM) and ferrous sulfate (5 μM) were added to and allowed to react with a rat liver microsomal preparation. The amount of peroxide thus formed was measured according to the thiobarbituric acid (TBA) method and the concentration of the compound under test required to inhibit the formation of lipid peroxide by 50% ($I_{50}$ μg/ml) was calculated. The results are reported in Table 3, below. The compounds of the invention are identified by the number of the Example in which their preparation is illustrated.

TABLE 3

| Example No. | Concentration inhibiting 50% of the lipid peroxide formation (μg/ml) |
|---|---|
| 2 | 0.03–0.1 |
| 3 | 0.03–0.1 |

The results shown above demonstrate that the compounds of the present invention strongly inhibit the formation of lipid peroxide, even at low concentrations.

We claim:

1. A compound of formula (I):

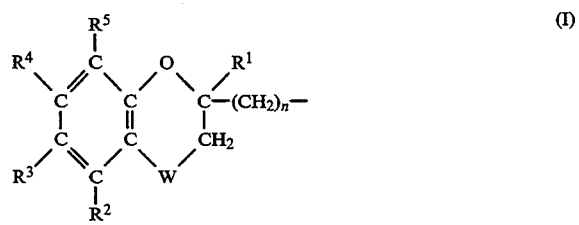

-continued

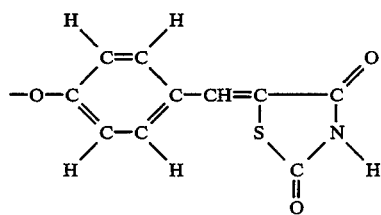

wherein $R^1$, R2, $R^4$ and $R^5$ are each methyl;
$R^3$ is hydroxy or acetoxy;
W is methylene; and
n is 1.

2. The compound of claim 1, wherein $R^3$ is hydroxy.

3. The compound of claim 1, wherein $R^3$ is acetoxy.

4. A pharmaceutical composition for the treatment or prophylaxis of diseases and disorders arising from an imbalance in the lipid peroxide level, said composition comprising an effective amount of an active compound of formula(I) or a pharmaceutically acceptable salt thereof, as claimed in claim 1, in admixture with a pharmaceutically acceptable carrier or diluent.

5. A method of reducing lipid peroxide levels in an animal by administering to said animal an effective amount of an active compound, wherein said active compound is selected from the group consisting of compounds of formula (I), as claimed in claim 1, and pharmaceutically acceptable salts thereof.

* * * * *